(12) United States Patent
Hochman

(10) Patent No.: US 7,214,711 B2
(45) Date of Patent: May 8, 2007

(54) METHOD OF TREATING MIGRAINE HEADACHE WITHOUT AURA

(75) Inventor: Daryl W. Hochman, Bahama, NC (US)

(73) Assignee: NeuroTherapeutics Pharma LLC, Seattle, WA (US)

( * ) Notice: Subject to any disclaimer, the term of this patent is extended or adjusted under 35 U.S.C. 154(b) by 49 days.

(21) Appl. No.: 10/056,528

(22) Filed: Jan. 23, 2002

(65) Prior Publication Data

US 2002/0082252 A1 Jun. 27, 2002

Related U.S. Application Data

(63) Continuation-in-part of application No. 09/470,637, filed on Dec. 22, 1999, now Pat. No. 6,495,601.

(60) Provisional application No. 60/263,830, filed on Jan. 23, 2001, provisional application No. 60/113,620, filed on Dec. 23, 1998.

(51) Int. Cl.
*A61K 31/195* (2006.01)
*A61K 31/18* (2006.01)

(52) U.S. Cl. ..................... 514/562; 514/603

(58) Field of Classification Search ............... 514/562, 514/603, 269
See application file for complete search history.

(56) References Cited

U.S. PATENT DOCUMENTS

| | | | | |
|---|---|---|---|---|
| 5,256,687 A | * | 10/1993 | Becker et al. | 514/419 |
| 5,475,008 A | * | 12/1995 | Carling et al. | 514/312 |
| 5,753,651 A | * | 5/1998 | dePadova | 514/223.5 |
| 6,040,331 A | * | 3/2000 | Yamamoto et al. | 514/411 |
| 6,130,234 A | * | 10/2000 | Bigge et al. | 514/322 |
| 6,369,094 B1 | * | 4/2002 | Bentley et al. | 514/414 |
| 6,432,986 B2 | * | 8/2002 | Levin | 514/330 |
| 6,669,951 B2 | * | 12/2003 | Rothbard et al. | 424/436 |

OTHER PUBLICATIONS

"Treatment of a Prolonged Migrainous Aura with Intravenous Furosemide", Rosen, T.D., Sep. 2000, Neurology:55, 732-733.*
"Acetazolamide Testing of Cerebral Vasodilator Capacity Provokes "Vascular" But Not Tension Headaches", Shirai et al., abstract, The Journal of Head and Face Pain, vol. 36, Issue. 10 p. 589, Nov. 1996.*
Strategies For Optimizing Migraine Management, Proceedings From A CME Teleconference Series, Sep. 10-14, 2001, pp. 1-26, especially p. 8, para. 5).*
"The Migraineur's Guide to Migraine, http://www.headachecare.com", 2000.*
"Topiramate Inhibits Cortical Spreading Depression in Rat and Cat: Impact in Migraine Aura", Akerman et al., abstract, Neuroreport, Aug. 22, 2005, 16(12):1383-7.*
"Primay Structure and Functional Expression of a cDNA Encoding the Thiazide-Sensitive, Electroneutral Sodium-Chloride Cotransporter", Gamba et al., Proc. Natl. Acad, Sci, USA, vol. 90, pp. 2749-2753, Apr. 1993.*
"Cortical Spreading Depression Reduces Dural Blood Flow—a Possible Mechanism for Migraine Pain", Lambert et al., abstract, Cephalalgia, Dec. 1994, 14(6):430-6; discussion 393-4.*
Read, S.J., et al., "Furosemide inhibits regenerative cortical spreading depression in anaesthetized cats", *Cephalalgia*, vol. 17, pp. 826-832 (1997).
Mathew, Ninan T., et al., "Coexistence of migraine and idiopathic intracranial hypertension without papilledema", *Neurologyl*, vol. 46, pp. 1226-1230 (May 1996).
Welch, K.M.A., M.D., "Pathogenesis of Migraine", *Seminars in Neurology*, vol. 17, No. 4, pp. 335-341 (1997).
Parsons, Andrew W., "Recent advances in mechanisms of spreading depression," *Current Opinion in Neurology*, vol. 11, pp. 227-231 (1998).
Snow, Robert W., et al., "Electrophysiological and Optical Changes in Slices of Rat Hippocampus During Spreading Depression," *Journal of Neurophysiology*, vol. 50, No. 3, pp. 561-572 (Sep. 1983).
Walz, Wolfgang et al., "Intense Furosemide-Sensitive Potassium Accumulation in Astrocytes in the Presence of Pathologically High Extracellular Potassium Levels," *Journal of Cerebral Blood Flow and Metabolism*, vol. 4, pp. 301-304 (1984).
Kimelberg, H.K. et al., "Furosemide- and bumetanide-sensitive ion transport and volume control in primary astrocyte cultures from rat brain," *ABSTRACT—Brain Res.*, vol. 361, Nos. 1-2, pp. 125-134 (Dec. 30, 1985).
Kimelberg, H.K., "Anisotonic media and glutamate-induced ion transport and volume responses in primary astrocyte cultures," *ABSTRACT—J. Physiol.* (Paris), vol. 82, Nos. 4, pp. 294-303 (1987).

(Continued)

*Primary Examiner*—Brian Kwon
(74) *Attorney, Agent, or Firm*—Speckman Law Group PLLC; Ann W. Speckman; Janet Sleath

(57) ABSTRACT

The present invention relates to methods and compositions for treating selected conditions of the central and peripheral nervous systems employing non-synaptic mechanisms. More specifically, one aspect of the present invention relates to methods and materials for treating seizure and seizure disorders, epilepsy, status epilepticus, migraine, spreading depression, intracranial hypertension; for treating the pathophysiological effects of head trauma, stroke, ischemia and hypoxia; for treating or protecting from the pathophysiological effects of neurotoxic agents such as ethanol; and for treating neurophsyciatric disorders and central nervous system edema by administering agents that modulate ionic concentrations and/or ionic gradients in the brain, particularly ion-dependent or cation-chloride cotransporter antagonists. Electrolyte cotransport antagonists and combinations of such compositions with other agents for treating various conditions are disclosed. The present invention also relates to methods and compositions for treating pain by administering ion-dependent cotransporter antagonists. Methods and compositions for enhancing cortical function, for example, in centers of cognition, learning and memory, by administering ion-dependent cotransporter agonists are disclosed.

8 Claims, 8 Drawing Sheets

OTHER PUBLICATIONS

Kempski, O. et al., "Glial ion transport and volume control," *ABSTRACT—Ann N.Y. Acad. Sci.*, vol. 633, pp. 306-317 (1991).

Walz, W., "Role of Na/K/Cl cotransport in astrocytes," *ABSTRACT—Can. J. Physiol. Pharmacol.*, vol. 70, Suppl., pp. S260-S262 (1992).

Walz, W., "Role of astrocytes in the spreading depression signal between ischemic core and penumbra," *ABSTRACT—Neurosci. Biobehav. Rev.*, vol. 21, No. 2., pp. 135-142 (1997).

Hochman, Daryl W., et al., "Extracellular Chloride and the Maintenance of Epileptiform Activity in Hippocampal Slices," *ABSTRACT—Society for Neuroscience*, vol. 23, Part 2., p. 2425 (1997).

Sinha, S.R., et al., "Effects of Furosemide on Normal and Epileptiform Evoked Activity in Area CA1 of Guinea Pig Hippocampal Slice," *ABSTRACT—Society for Neuroscience*, vol. 23, Part 2., p. 2425 (1997).

Collins, Michael A., et al., "Brian damage due to episodic alcohol exposure in vivo and in vitro: furosemide neuroprotection implicates edema-based mechanism," *The FASEB Journal*, vol. 12, pp. 221-230 (Feb. 1998).

Hochman, Daryl W., et al., "Dissociation of Synchronization and Excitability of Furosemide Blockade of Epileptiform Activity," *Science*, vol. 270, pp. 99-102 (Oct. 6, 1995).

Pinegin, L.E., et al., "Effect of furosemide on intracranial pressure in patients with intracranial hypertension," *ABSTRACT—Medline* (1983).

Misiuk, N.S., et al., "Effect of glycerol, mannitol and lasix on cerebrospinal fluid pressure in the acute period of a stroke," *ABSTRACT—Medline* (1981).

* cited by examiner

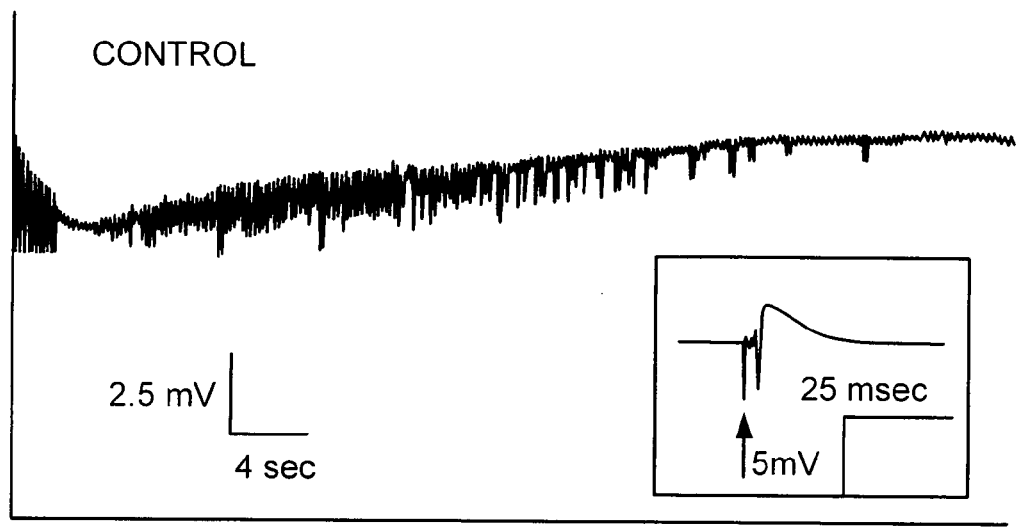
FIG. 1A
FIG. 1A1

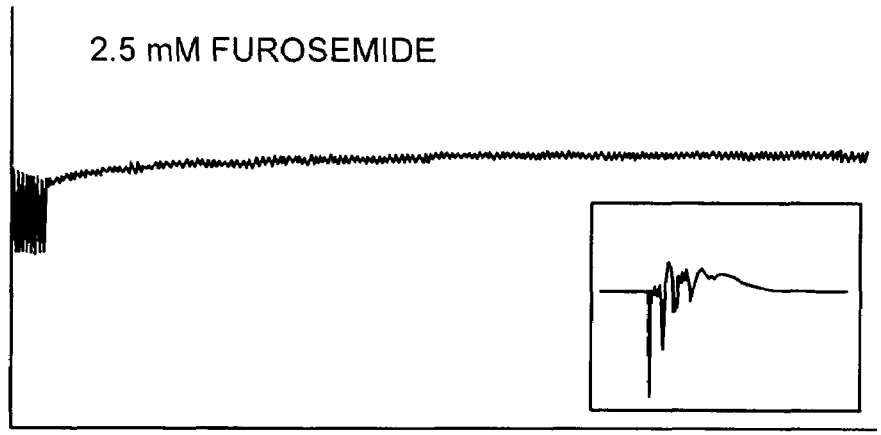
FIG. 1B
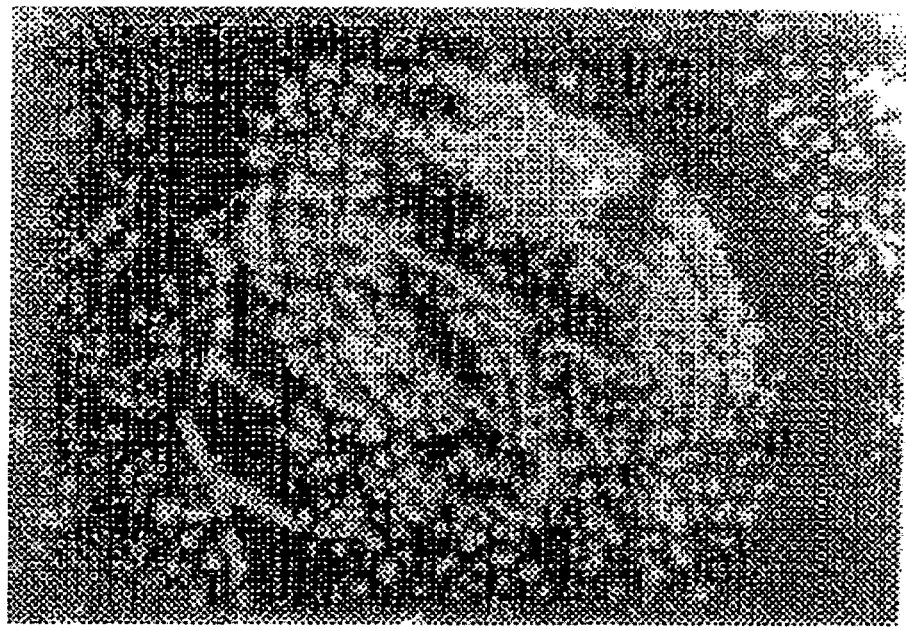
FIG. 1B1

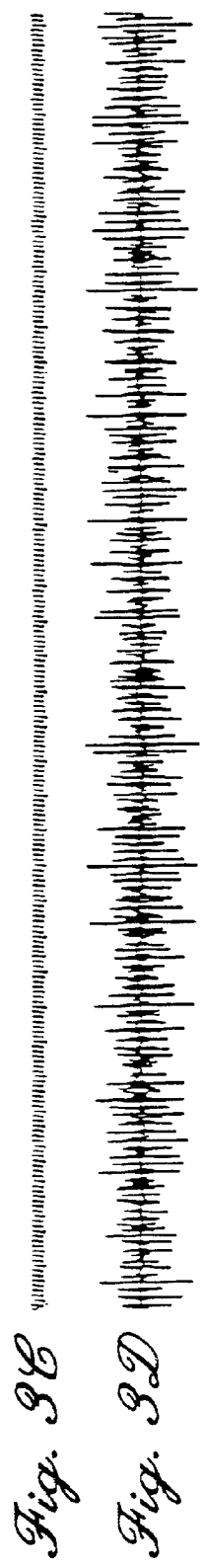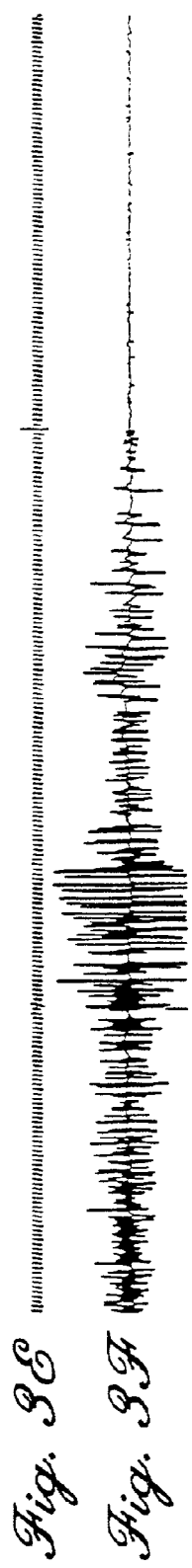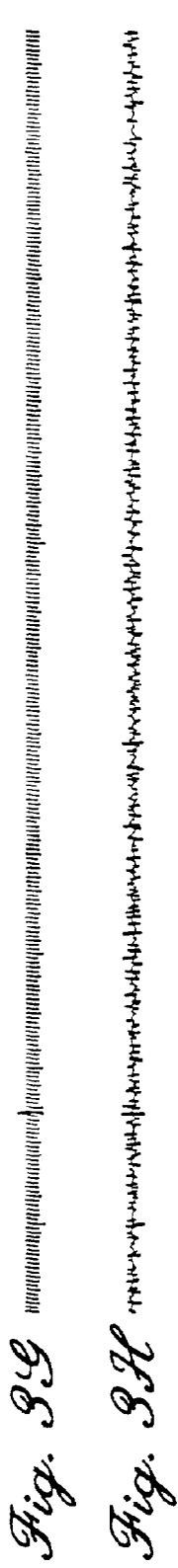
Fig. 3A
Fig. 3B
Fig. 3C
Fig. 3D
Fig. 3E
Fig. 3F
Fig. 3G
Fig. 3H

US 7,214,711 B2

METHOD OF TREATING MIGRAINE HEADACHE WITHOUT AURA

REFERENCE TO RELATED AND PRIORITY APPLICATIONS

This application claims priority to U.S. patent application Ser. No. 60/263,830, filed Jan. 23, 2001 under 35 U.S.C. 119(e). This application is a continuation-in-part of U.S. patent application Ser. No. 09/470,637, filed Dec. 22, 1999, U.S. Pat. No. 6,495,601 which claims priority to U.S. patent application Ser. No. 60/113,620, filed Dec. 23, 1998 under 35 U.S.C. 119(e).

TECHNICAL FIELD OF THE INVENTION

The present invention relates to methods and compositions for treating selected conditions of the central and peripheral nervous systems employing non-synaptic mechanisms. More specifically, one aspect of the present invention relates to methods and compositions for treating seizures and seizure disorders, epilepsy, status epilepticus, migraine headache, cortical spreading depression, intracranial hypertension, neuropsychiatric disorders, central nervous system edema; for treating or protecting from the pathophysiological effects of toxic agents such as ethanol and certain infectious agents; for treating the pathophysiological effects of head trauma, stroke, ischemia and hypoxia; and for improving certain brain functions, such as cognition, learning and memory; by administering agents that modulate ionic concentrations and ionic balances in the central nervous system. Specific treatment compositions, including loop diuretics, thiazide-like diuretics, analogs and derivatives of such compositions, as well as combinations of such compositions with other agents for modulating ionic concentrations and gradients, and for treating various conditions, are disclosed. Compositions and methods for treating pain by administering agents that modulate ionic concentrations and gradients in the peripheral nervous system are also disclosed.

BACKGROUND OF THE INVENTION

Conventional treatments for neuronal disorders, such as seizure disorders, epilepsy, and the like, target synaptic mechanisms that affect excitatory pathways, such as by modulating the release or activity of neurotransmitters or inhibitors. Conventional treatment agents and regimen for seizure disorders diminish neuronal excitability and inhibit synaptic firing. One serious drawback of this approach is that while seizures are generally localized, the treatment affects (diminishes) neuronal activity indiscriminately. For this reason, there are serious side effects and repeated use of conventional medications may result in unintended deficiencies in normal and desirable brain functions, such as cognition, learning and memory. More detailed information concerning particular disorders of interest is provided below.

Epilepsy

Epilepsy is characterized by abnormal discharges of cerebral neurons and typically manifested as various types of seizures. Epileptiform activity is identified with spontaneously occurring synchronized discharges of neuronal populations that can be measured using electrophysiological techniques. This synchronized activity, which distinguishes epileptiform from non-epileptiform activity, is referred to as "hypersynchronization" because it describes the state in which individual neurons become increasingly likely to discharge in a time-locked manner with one another.

Epilepsy is one of the most common neurological disorders, affecting about 1% of the population. There are various forms of epilepsy, including idiopathic, symptomatic and cryptogenic. Genetic predisposition is thought to be the predominant etiologic factor in idiopathic epilepsy. Symptomatic epilepsy usually develops as a result of a structural abnormality in the brain.

Status epilepticus is a particularly severe form of seizure, which is manifested as multiple seizures that persist for a significant length of time, or serial seizures without any recovery of consciousness between seizures. The overall mortality rate among adults with status epilepticus is approximately 20 percent. Patients who have a first episode are at substantial risk for future episodes and the development of chronic epilepsy. The frequency of status epilepticus in the United States is approximately 150,000 cases per year, and roughly 55,000 deaths are associated with status epilepticus annually. Acute processes that are associated with status epilepticus include intractable epilepsy, metabolic disturbances (e.g. electrolyte abnormalities, renal failure and sepsis), central nervous system infection (meningitis or encephalitis), stroke, degenerative diseases, head trauma, drug toxicity and hypoxia. The fundamental pathophysiology of status epilepticus involves a failure of mechanisms that normally abort an isolated seizure. This failure can arise from abnormally persistent, excessive excitation or ineffective recruitment of inhibition. Studies have shown that excessive activation of excitatory amino acid receptors can cause prolonged seizures and suggest that excitatory amino acids may play a causative role. Status epilepticus can also be caused by penicillin and related compounds that antagonize the effects of γ-aminobutyric acid (GABA), the primary inhibitory neurotransmitter in the brain.

One early diagnostic procedure for epilepsy involved the oral administration of large quantities of water together with injections of vasopressin to prevent the accompanying diuresis. This treatment was found to induce seizures in epileptic patients, but rarely in non-epileptic individuals (Garland et al., *Lancet*, 2:566, 1943). Status epilepticus can be blocked in kainic acid-treated rats by intravenous injection of mannitol (Baran et al., *Neuroscience*, 21:679, 1987). This effect is similar to that achieved by intravenous injection of urea in human patients (Carter, *Epilepsia*, 3:198, 1962). The treatment in each of these cases increases the osmolarity of the blood and extracellular fluid, resulting in water efflux from the cells and an increase in extracellular space in the brain. Acetazolamide (ACZ), another diuretic with a different mechanism of action (inhibition of carbonic anhydrase), has been studied experimentally as an anticonvulsant (White et al., *Advance Neurol.*, 44:695, 1986; and Guillaume et al., *Epilepsia*, 32:10, 1991) and used clinically on a limited basis (Tanimukai et al., *Biochem. Pharm.*, 14:961, 1965; and Forsythe et al., *Develop. Med. Child Neurol.*, 23:761, 1981). Although its mechanism of anticonvulsant action has not been determined, ACZ does have a clear effect on the cerebral extracellular space.

Traditional anti-epileptic drugs exert their principal effect through one of three mechanisms: (a) inhibition of repetitive, high-frequency neuronal firing by blocking voltage-dependent sodium channels; (b) potentiation of γ-aminobutyric acid (GABA)-mediated postsynaptic inhibition; and (c) blockade of T-type calcium channels. Phenytoin and carbamazepine are examples of sodium channel antagonists, which exert their effect at the cellular level by reducing or eliminating sustained high-frequency neuronal depolarization while not appreciably affecting regular firing rates of neurons. Barbiturates, such as Phenobarbital and benzodiazepines, act by enhancing GABA-mediated synaptic inhibition. Both classes of compounds increase the hyperpolarization of the postsynaptic membrane, resulting in increased inhibition. Ethosuximide and valporate are examples of drugs that decrease calcium entry into neurons through T-type voltage-dependent calcium channels.

Current anti-epileptic drug therapies exert their pharmacological effects on all brain cells, regardless of their involvement in seizure activity. Common side effects are over-sedation, dizziness, loss of memory and liver damage. Additionally, 20–30% of epilepsy patients are refractory to current therapy.

Focus on synaptic hyperexcitability has been a guiding principle in basic research on the mechanisms of epileptogenesis and in the design and discovery of new anti-epileptic drugs. One of the shortcomings of this approach is that most current anti-epilepsy drugs exert their influence in an indiscriminate manner, in both the epileptogenic and normal areas in the brain. The compositions of the present invention offer a novel approach to the treatment of seizures, in part because they act via a non-synaptic pathway.

Migraine

Migraine headaches afflict 10–20% of the U.S. population, with an estimated loss of 64 million workdays annually. Migraine headache is characterized by pulsating head pain that is episodic, unilateral or bilateral, lasting from 4 to 72 hours and often associated with nausea, vomiting and hypersensitivity to light and/or sound. When accompanied by premonitory symptoms, such as visual, sensory, speech or motor symptoms, the headache is referred to as "migraine with aura," formerly known as classic migraine. When not accompanied by such symptoms, the headache is referred to as "migraine without aura," formerly known as common migraine. Both types evidence a strong genetic component, and both are three times more common in women than men. The precise etiology of migraine has yet to be determined. It is theorized that persons prone to migraine have a reduced threshold for neuronal excitability, possibly due to reduced activity of the inhibitory neurotransmitter γ-aminobutyric acid (GABA). GABA normally inhibits the activity of the neurotransmitters serotonin (5-HT) and glutamate, both of which appear to be involved in migraine attacks. The excitatory neurotransmitter glutamate is implicated in an electrical phenomenon called cortical spreading depression, which can initiate a migraine attack, while serotonin is implicated in vascular changes that occur as the migraine progresses.

Cortical spreading depression (CSD) is characterized by a short burst of intense depolarization in the occipital cortex, followed by a wave of neuronal silence and diminished evoked potentials that advance anteriorly across the surface of the cerebral cortex. Enhanced excitability of the occipital-cortex neurons has been proposed as the basis for CSD. The visual cortex may have a lower threshold for excitability and therefore is most prone to CSD. Mitochondrial disorders, magnesium deficiency and abnormality of presynaptic calcium channels may be responsible for neuronal hyperexcitability (Welch, K. M. A., Pathogenesis of Migraine, *Seminars in Neurobiology*, vol. 17:4, 1997). During a spreading depression event, profound ionic perturbations occur, which include interstitial acidification, extracellular potassium accumulation and redistribution of sodium and chloride ions to intracellular compartments. In addition, prolonged glial swelling occurs as a homeostatic response to altered ionic extracellular fluid composition and interstitial neurotransmitter and fatty acid accumulation. Studies have shown that furosemide inhibits regenerative cortical spreading depression in anaesthetized cats (Read, S J, et al, *Cephalagia*, 17:826, 1997).

A study of eighty-five patients with refractory transformed migraine type of chronic daily headache (CDH) concluded that acute headache exacerbations responded to specific anti-migraine agents such as ergotamine, dihydroergotamine (DHE), and sumatriptan, and addition of agents such as acetazolamide and furosemide, after diagnosis of increased intracranial pressure, resulted in better control of symptoms (Mathew, N. T. et al. Neurology 46:(5), 1226–1230, May 1996). The authors note that these results suggest a link between migraine and idiopathic intracranial hypertension that needs further research. It has also been reported that furosemide appeared to abort prolonged visual auras in two migraine patients. The author speculated that furosemide may act to inhibit CSD activity. (Rozen, T. D. Neurology 55(5): 732–3 (2000).

Drug therapy is tailored to the severity and frequency of migraine headaches. For occasional attacks, abortive treatment may be indicated, but for attacks occurring two or more times per month, or when attacks greatly impact the patient's daily life, prophylactic therapy may be indicated. Serotonin receptor agonists, such as sumatriptan, have been prescribed for abortive therapy. Serotonin receptor agonists are thought to constrict dilated arteries of the brain and thereby alleviate the associated pain. Side effects associated with this therapy include tingling, dizziness, warm-hot sensation, and injection-site reactions. Intravenous administration is contraindicated as a consequence of the potential for coronary vasopasms. Ergotamine-based drugs are classified as vasoconstrictors that specifically counteract the dilation of some arteries and arterioles, primarily the branches of the external carotid artery. To prevent ergotamine rebound phenomena, ergotamine should not be repeated on the second or third day of a migraine attack. Yet, if the drug is stopped abruptly, the patient will experience a severe rebound headache. Excessive consumption of ergotamines may cause symptoms of vasoconstriction, such as cold clammy extremities, and may lead to ergotism.

Drugs used for prophylactic indications include andrenergic beta-blockers such as propranolol, calcium channel blockers, or low-dose anti-epileptics. In particular, antiepileptic drugs that increase brain levels of GABA, either by increasing GABA synthesis or reducing its breakdown, appear to be effective in preventing migraine in certain individuals. In some patients, tricyclic analgesics, such as amitriptline, can be effective. NMDA receptor antagonist, acting at one of the glutamate receptor subtypes in the brain, inhibits CSD. Drugs or substances currently believed to function as weak NMDA receptor antagonists include dextromethoraphan, magnesium and ketamine. Intravenous magnesium has been successfully used to abort migraine attacks.

Neurotoxicity

A variety of chemical and biological agents, as well as some infectious agents, have neurotoxic effects. A common example is the pathophysiological effect of acute ethanol ingestion. Episodic ethanol intoxications and withdrawals characteristic of binge alcoholism result in brain damage. Animal models designed to mimic the effects of alcohol in the human have demonstrated that a single dose of ethanol given for 5–10 successive days results in neurodegeneration in the entorhinal cortex, dentate gyrus and olfactory bulbs, accompanied by cerebrocortical edema and electrolyte ($Na^+$ and $K^+$) accumulation. As with other neurodegenerative conditions, research has focused primarily on synaptically based excitotoxic events involving excessive glutamatergic activity, increased intracellular calcium and decreased γ-aminobutyric acid. Co-treatment of brain damage induced by episodic alcohol exposure with an NMDA receptor antagonist, Non-NMDA receptor and $Ca^{2+}$ channel antagonists with furosemide reduces alcohol-dependent cerebrocortical damage by 75–85%, while preventing brain hydration and electrolyte elevations (Collins, M., et al, FASEB, vol. Feb. 12, 1998). The authors observed that the results suggest that furosemide and related agents might be useful as neuroprotective agents in alcohol abuse.

Cognition, Learning and Memory

The cognitive abilities of mammals are thought to be dependent on cortical processing. It has generally been accepted that the most relevant parameters for describing and understanding cortical function are the spatio-temporal patterns of activity. In particular, long-term potentiation and long-term depression have been implicated in memory and learning and may play a role in cognition. Oscillatory and synchronized activities in the brains of mammals have been correlated with distinct behavioral states.

Synchronization of spontaneous neuronal firing activity is thought to be an important feature of a number of normal and pathophysiological processes in the central nervous system. Examples include synchronized oscillations of population activity such as gamma rhythms in the neocortex, which are thought to be involved in cognition (Singer and Gray, 1995), and theta rhythm in hippocampus, which is thought to play roles in spatial memory and in the induction of synaptic plasticity (Heurta and Lisman 1995; Heurta and Lisman 1996; O'keefe 1993). To date, most research on the processes underlying the generation and maintenance of spontaneous synchronized activity has focused on synaptic mechanisms. However, there is evidence that nonsynaptic mechanisms may also play important roles in the modulation of synchronization in normal and pathological activities in the central nervous system.

Screening of Candidate Compounds and Evaluating Treatment Efficacy

Drug development programs rely on in vitro screening assays and subsequent testing in appropriate animal models to evaluate drug candidates prior to conducting clinical trials using human subjects. Screening methods currently used are generally difficult to scale up to provide the high throughput screening necessary to test the numerous candidate compounds generated by traditional and computational means. Moreover, studies involving cell culture systems and animal model responses frequently don't accurately predict the responses and side effects observed during human clinical trials.

Conventional methods for assessing the effects of various agents or physiological activities on biological materials, in both in vitro and in vivo systems, generally are not highly sensitive or informative. For example, assessment of the effect of a physiological agent, such as a drug, on a population of cells or tissue grown in culture, conventionally provides information relating to the effect of the agent on the cell or tissue population only at specific points in time. Additionally, current assessment techniques generally provide information relating to a single or a small number of parameters. Candidate agents are systematically tested for cytotoxicity, which may be determined as a function of concentration. A population of cells is treated and, at one or several time points following treatment, cell survival is measured. Cytotoxicity assays generally do not provide any information relating to the cause(s) or time course of cell death.

Similarly, agents are frequently evaluated based on their physiological effects, for example, on a particular metabolic function or metabolite. An agent is administered to a population of cells or a tissue sample, and the metabolic function or metabolite of interest is assayed to assess the effect of the agent. This type of assay provides useful information, but it does not provide information relating to the mechanism of action, the effect on other metabolites or metabolic functions, the time course of the physiological effect, general cell or tissue health, or the like.

U.S. Pat. Nos. 5,902,732 and 5,976,825, disclose methods for screening drug candidate compounds for anti-epileptic activity using glial cells in culture by osomotically shocking glial cells, introducing a drug candidate, and assessing whether the drug candidate is capable of abating changes in glial cell swelling. These patents also disclose a method for screening drug candidate compounds for activity to prevent or treat symptoms of Alzheimer's disease, or to prevent CNS damage resulting from ischemia, by adding a sensitization agent capable of inducing apoptosis and an osmotic stressing agent to CNS cells, adding the drug candidate, and assessing whether the drug candidate is capable of abating cell swelling. A method for determining the viability and health of living cells inside polymeric tissue implants is also disclosed, involving measuring dimensions of living cells inside the polymeric matrix, osmotically shocking the cells, and then assessing changes in cell swelling. Assessment of cell swelling activity is achieved by measuring intrinsic optical signals using an optical detection system. U.S. Pat. Nos. 6,096,510 and 6,319,682 disclose additional methods for screening drug candidate compounds.

SUMMARY OF THE INVENTION

Selected treatment compositions and methods of the present invention are useful for treating central nervous system conditions, including seizures and seizure disorders, epilepsy, including Status epilepticus, migraine headaches, other types of headaches, cortical spreading depression, intracranial hypertension, neuropsychiatric disorders, and central nervous system edema. Selected treatment compositions and methods of the present invention are also suitable for treating or protecting from the pathophysiological effects of neurotoxic agents such as ethanol and certain infectious agents, and for treating the pathophysiological effects of head trauma, stroke, ischemia and hypoxia. According to another embodiment, treatment agents and methods of the present invention improve function in certain cortical tissue, such as in cortical centers of cognition, learning and memory. Additionally, treatment agents and methods of the present invention are useful for treating pain by affecting or modulating the conduction of impulses associated with pain in the peripheral nervous system. Treatment compositions and methods of the present invention may be used therapeutically and episodically following the onset of symptoms, or prophylactically prior to the onset of specific symptoms, and are suitable for both human and veterinary applications.

Methods and compositions of the present invention, in one aspect, involve treatment of various conditions of the central and peripheral nervous systems via non-synaptic mechanisms and, more specifically, by modulating, generally reducing, the synchronization of neuronal population activity. According to a preferred embodiment, the synchronization of neuronal population activity is modulated by manipulating anionic concentrations and gradients in the central and/or peripheral nervous systems. Ion dependent cotransporter antagonists are suitable treatment compositions, anion cotransporter antagonists are preferred treatment compositions, and cation-chloride cotransporter antagonists are especially preferred treatment compositions. According to one embodiment, $Na^+$, $K^+$, $2Cl^-$ chloride cotransporter antagonists are especially preferred treatment agents for modulating the synchronization of neuronal population activity. Anion cotransporter antagonists are useful for treating conditions such as seizures, epilepsy and status epilepticus, cortical spreading depression, migraine and other types of headaches, intracranial hypertension, neuropsychiatric disorders, central nervous system edema, for treating or protecting from the pathophysiological effects of neurotoxic agents such as ethanol and certain infectious agents, and for reducing the perception of pain. Chloride cotransporter agonists are preferred treatment agents, and cation-chloride cotransporter agonists are especially preferred treatment agents for improving function in cortical areas associated with cognition, learning and memory, for example.

Reference to the preferred methods and anion cotransporter antagonist treatment agents of the present invention using "non-synaptic" mechanisms means that mechanisms associated with neuronal excitability, such as the release or activity of transmitters, or the release or activity of inhibitors, are not substantially affected by the methods or administration of anion cotransporter antagonist treatment agents of the present invention. For example, use of methods or administration of an anion cotransporter antagonist treatment agent of the present invention produces no more than a 30% change in the release or activity of excitatory or inhibitory transmitters, compared as pre-administration and post-administration levels or activities. Similarly, ion channels and receptors are not directly affected by methods and anion cotransporter antagonist treatment agents of the present invention. Rather, the methods and anion cotransporter antagonist treatment agents of the present invention affect the synchronization, or relative synchrony, of neuronal population activity. Preferred methods and anion cotransporter antagonist treatment agents of the present invention modulate the extracellular anionic chloride concentration and/or the gradients in the central or peripheral nervous system to modulate (reduce) neuronal synchronization, or relative synchrony, without substantially affecting neuronal excitability. Combination of an ion-dependent iotransporter antagonist with another treatment agent, as described below, may involve both synaptic and non-synaptic mechanisms.

One aspect of the present invention relates to treatment agents and methods for modulating the synchronization of neuronal discharges by diminishing or eliminating hypersynchronization of neuronal population activity associated with seizures, migraine headaches, cortical spreading depression, and other pathophysiologies of the central nervous system. In one embodiment, the treatment composition is capable of modulating the anion concentration, preferably the chloride concentration, in the extracellular space in the central nervous system. In a preferred embodiment, the treatment agent is a chloride cotransporter antagonist. In another preferred embodiment, the treatment agent is a cation chloride cotransporter antagonist, and in an especially preferred embodiment, the treatment composition is a glial cell $Na^+$, $K^+$,$2Cl^-$ cotransporter antagonist. According to yet another preferred embodiment, the treatment agent has a high level of cation-chloride cotransporter antagonist activity in glial cells, and has a lower level of ion-dependent cotransporter activity in neuronal and kidney cells. Preferred agents for treatment of central nervous system conditions are preferably capable of crossing the blood brain barrier, or are administered using delivery systems that facilitate delivery of agents to the central nervous system. Various blood brain barrier (BBB) permeability enhancers can be used, if desired, to transiently and reversibly increase the permeability of the blood brain barrier to an ion dependent cotransporter antagonist. Such BBB permeability enhancers may include leukotrienes, bradykinin agonists, histamine, tight junction disruptors (e.g., zonulin, zot), hyperosmotic solutions (e.g., mannitol), cytoskeletal contracting agents, short chain alkylglycerols (e.g., 1-O-pentylglycerol), and others. In general, loop diuretics, such as furosemide, bumetanide, ethacrinic acid, and the like, as well as thiazide and thiazide-like diuretics, exhibit ion-dependent cotransporter antagonist activity and are suitable for use as treatment compositions of the present invention. Although such loop diuretics produce the desired modulation of the extracellular anionic chloride concentrations and ionic gradients and, hence, modulation of synchronization of neuronal population activity, they may also produce other, undesired effects. Furosemide, for example, acts as a cation-chloride cotransporter antagonist in both glial and neuronal cells, as well as in the kidney. Especially preferred treatment agents of the present invention, exhibiting ion-dependent cotransporter antagonist activity, exhibit a high degree of activity in glial cell populations, and exhibit a lesser degree of activity in neuronal and renal cell populations.

In another aspect, methods and compositions of the present invention involve the use of combinations of agents, particularly the combination of an agent employing a non-synaptic mechanism, such as an ion-dependent cotransporter antagonist, with one or more agents employing one or more traditional treatment mechanism(s). Methods for treating seizure disorders and status epilepticus involve administering an ion-dependent cotransporter antagonist, preferably a cation-chloride cotransporter antagonist, in combination with another treatment agent. Furosemide and other loop diuretics, as well as thiazide and thiazide-like diuretics, are suitable cation-chloride cotransporter antagonists. Experimental studies have shown that furosemide treatment produces a transient and early increase in synchronization of neuronal population activity, followed by a persistent and complete disruption of the hypersynchronization characteristic of epileptiform activity. Treatment of status epilepticus, according to one embodiment of the present invention, involves administration of an agent that affects the synchronization, or relative synchrony, of neuronal population activity, such as an ion-dependent cotransporter antagonist, preferably a cation-chloride cotransporter antagonist such as furosemide or a furosemide-related compound or thiazide or thiazide-like compund, in combination with another agent that may affect a synaptic mechanism, such as a barbiturate, that is capable of treating the symptoms associated with the transient and early increase in synchronization of neuronal population activity observed upon administration of an ion-dependant cotransporter antagonist. In one embodiment, the above-mentioned combination therapy will include the acute administration of a pharmaceutically acceptable hyperosmotic agent, such as mannitol, for enhanced effect.

In another embodiment, materials and methods of the present invention are used to treat migraine headaches and its precursor condition, cortical spreading depression (CSD), as well as other types of head ache conditions. During spreading depression, profound ionic perturbations occur, which include interstitial acidification, extracellular potassium accumulation and redistribution of sodium and chloride ions to intracellular compartments. In addition, prolonged glial swelling occurs as a homeostatic response to altered ionic extracellular fluid composition and interstitial neurotransmitter and fatty acid accumulation. Materials and methods of the present invention inhibit the generation and duration of CSD by blocking the inward sodium-dependent movement of chloride ions mediated by the chloride-dependent cotransporters. Treatment compositions of the present invention for treating migraine headaches and cortical spreading depression comprise cation-chloride cotransporter antagonists, such as furosemide, furosemide-like compounds, thiazide and thiazide-like diuretic compounds. According to a preferred embodiment, agents and methods of the present invention for treating migraine headaches and cortical spreading depression preferentially act on the $Na^+$, $K^+$, $2Cl^-$ chloride-dependent cotransport system of glial cells and have reduced activity on the chloride-dependent cotransport systems of other cell types, particularly neurons and renal cells. Treatment compositions comprising cation-chloride cotransporter antagoinists may also be administered, in combination with other compositions, to treat or prevent various headache conditions, as described in greater detail below. BBB permeability enhancers may also be used.

Methods and treatment compositions for treating seizures and seizure disorders, epilepsy, migraine and other headaches, cortical spreading depression, intracranial hypertension, neuropsychiatric disorders, and for treating or protecting from the pathophysiological effects of neurotoxic agents, head trauma, stroke, ischemia and hypoxia involve modulating the synchronization of neuronal population activity, preferably by modulating ion gradients in the central nervous system. Ion-dependent cotransporter antagonists are preferred treatment compositions, and cation-chloride cotransporter antagonists are especially preferred treatment compositions. Loop diuretics, loop-diuretic-related compounds, thiazides and thiazide-like diuretics are suitable ion-dependent cotransporter antagonists. Also contemplated for use in combination with ion-dependent cotransporter antagonists is a pharmaceutically acceptable hyperosmotic agent, such as hypertonic saline or mannitol. The combination is expected to be particularly efficacious for reducing brain swelling in traumatic head injury and cerebral edema, and is potentially useful as well for preventing the onset of convulsions in term infants with hypoxic-ischemic encephalopathy. If the ion-dependent cotransporter antagonist treatment composition has activity, for example, with respect to glial cells, but has lower or substantially no activity with respect to neuronal cells, it is suitable for administration alone. If the ion-dependent cotransporter antagonist treatment composition has activity with respect to neuronal as well as other types of cells, it is preferably administered in combination with another agent, such as conventional anti-epileptic or anti-convulsant agent.

Yet another aspect of the present invention involves treatment of neurotoxicity attributable to a variety of chemical and biological agents, as well as some infectious agents. Compositions and methods of the present invention are especially effective in reducing the neurodegenerative effects of acute ethanol ingestion. Additionally, compositions of the present invention may be administered prophylactically to protect cortical tissue from the effects of neurotoxicity attributable, for example, to acute ethanol ingestion. Treatment compositions of the present invention for treating, or for prophylactic administration to protect from neurotoxicity, comprise ion-dependent cotransporter antagonists, preferably cation-chloride cotransporter antagonists. According to a preferred embodiment, agents and methods of the present invention for protecting from neurotoxicity preferentially act on the $Na^+$, $K^+$, $2Cl^-$ chloride-dependent cotransport system of glial cells and have reduced activity on the chloride-dependent cotransport systems of other cells types, such as neurons and renal cells.

Another aspect of the present invention relates to methods and agents for relieving pain, or the perception of pain, by effecting or modulating propagation of action potentials or conduction of impulses in certain nerve fibers, particularly unmyelinated fibers, in the peripheral nervous system. More specifically, changes in extracellular ionic concentrations and ionic gradients in cells in the peripheral nervous system, affected by ion-dependent cotransporters, diminishes the perception or sensation of pain. Agents of the present invention for treating, or for prophylactic administration to protect from pain, ion-dependent chloride cotransporter antagonists, preferably cation-chloride transporter antagonists, that modulate the extracellular ionic concentration and/or the ionic gradients in the peripheral nervous system. According to a preferred embodiment, compositions of the present invention for treating pain preferentially act on the cation-chloride cotransport system of glial cells, or Schwantz cells, and have reduced activity on the chloride-dependent cotransport systems of other types of cells, such as neurons and renal cells.

Yet another aspect of the present invention relates to methods and agents for enhancing the function of certain cortical functions, such as, cognitive, learning and memory. Enhanced synchronization of neuronal population activity improves function in centers associated with cognitive abilities, learning and memory in central nervous system cortex. Treatment compositions and methods of the present invention for enhancing cognitive, learning and memory functions involve modulating the synchronization and timing of neuronal population activity, preferably by enhancing synchronization and coordinating timing. According to one embodiment, enhancement of synchronization is achieved by administering an agent capable of modulating extracellular anionic chloride concentrations and ionic gradients in the brain. Ion-dependent cotransporter agonists are preferred treatment agents, and cation-chloride cotransporter agonists are especially preferred. Methods for screening candidate compounds for ion-dependent cotransporter agonist activity are also provided.

Screening methods and systems for identifying treatment agents of the present invention preferably employ optical, or spectroscopic, detection techniques to assess the physiological state of biological materials including cells, tissues, organs, subcellular components and intact organisms. The biological materials may be of human, animal, or plant origin, or they may be derived from any such materials. Static and dynamic changes in the geometrical structure and/or intrinsic optical properties of the biological materials in response to the administration of a physiological challenge or a test agent, are indicative and predictive of changes in the physiological state or health of the biological material. Detailed descriptions of the screening methods are provided in U.S. Pat. Nos. 6,096,510, and 6,319,682, which are incorporated herein by reference in their entireties.

BRIEF DESCRIPTION OF THE DRAWINGS

FIGS. 1A, 1A1, 1B, 1B1, 1C, 1C1 and 1D show the effect of furosemide on stimulation evoked after discharge activity in rat hippocampal slices.

FIGS. 3A–3H show furosemide blockade of kainic acid-evoked electrical "status epilepticus" in urethane-anesthetized rats, with EKG recordings shown in the upper traces and cortical EEG recordings shown in the bottom traces.

DETAILED DESCRIPTION OF THE INVENTION

Figure 1C:
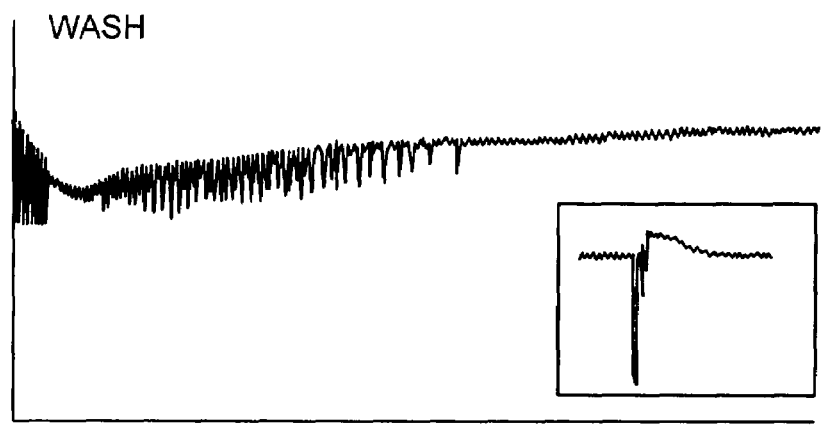

Preferred ion-dependent cotranporter antagonist treatment agents and methods of the present invention, for use in treating seizures and other pathophysiological disorders of the central nervous system, modulate or disrupt the synchrony of neuronal population activity in areas of heightened synchronization, such as epileptic foci. As described in detail below and illustrated in the examples, movement of ions and modulation of ionic gradients by means of ion-dependent cotransporters, preferably cation-chloride dependent cotranporters, is critical to regulation of neuronal synchronization. Chloride cotransport function has long been thought to be directed primarily to movement of chloride out of cells. The sodium independent transporter, which has been shown to be neuronally localized, moves chloride ions out of neurons. Blockade of this transporter, such as by administration of the loop diuretic furosemide, leads to hyperexcitability, which is the short-term response to cation-chloride cotransporters such as furosemide. However, the long-term response to furosemide demonstrates that the inward, sodium-dependent movement of chloride ions, mediated by the glial associated $Na^+$, $K^+$, $2Cl^-$ cotransporter, plays an active role in blocking neuronal synchronization and, hence, seizure, without affecting excitability and stimulus-evoked cellular activity.

Compositions of the subject invention are suitable for human and veterinary applications and are preferably delivered as pharmaceutical compositions. Pharmaceutical compositions comprise one or more treatment agents and a physiologically acceptable carrier. Pharmaceutical compositions of the present invention may also contain other compounds, which may be biologically active or inactive. For example, one or more compounds from the class of chloride cotransporter agonists or antagonists may be combined with another agent, in a treatment combination, and administered according to a treatment regimen of the present invention. Such combinations may be administered as separate compositions, or may be combined for delivery in a complementary delivery system, or may be formulated in a combined composition, such as a mixture or a fusion compound. Additionally, the aforementioned treatment combination may include a BBB permeability enhancer and/or a hyperosmotic agent.

While any suitable carrier known to those of ordinary skill in the art may be employed in the pharmaceutical compositions of this invention, the preferred carrier depends upon the preferred mode of administration. Compositions of the present invention may be formulated for any appropriate mode of administration, including for example, topical, oral, nasal, rectal, intravenous, intracranial, spinal tap, intraperitoneal, transdermal, subcutaneous or intramuscular administration. For parenteral administration, such as by subcutaneous injection, the carrier preferably comprises water, saline, glycerin, propylene glycol, alcohol, a fat, a wax and/or a buffer. For oral administration, any of the above carriers, or a solid carrier such as mannitol, lactose, starch, magnesium stearate, sodium lauryl sulphate, lactose, sodium citrate, calcium carbonate, calcium phosphate, silicates, polyethylene glycol, sodium saccharine, talcum, cellulose, glucose, sucrose, dyes, and magnesium carbonate, may be employed. For rectal administration, an aqueous gel formulation, or other suitable formulations that are well known in the art may be administered. Solid compositions may also be employed as fillers in soft and hard filled gelatin capsules. Preferred materials for this include lactose or mild sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

Local intracerebral administration, which reduces systemic distribution of the treatment composition(s), may be provided by perfusion via a mechanized delivery system, such as an osmotic pump, or by implantation of a dosage of the treatment composition(s) incorporated in a non-reactive carrier to provide controlled diffusion of the treatment composition over a time course to a circumscribed region of the brain. Other types of time release formulations may also be implemented. Additionally, direct intrathecal injection or administration into the cerebral spinal fluid via the spinal cord by injection, osmotic pump or other means is preferred for certain applications.

The compositions described herein may be administered as part of a sustained release formulation. Such formulations may generally be prepared using well-known technology and administered by, for example, oral, rectal or transdermal delivery systems, or by implantation of a formulation or therapeutic device at one or more desired target site(s). Sustained-release formulations may contain a treatment composition comprising an ion-dependent cotransporter agonist or antagonist alone, or in combination with a second treatment agent, dispersed in a carrier matrix and/or contained within a reservoir surrounded by a rate controlling membrane. Carriers for use within such formulations are biocompatible, and may also be biodegradable. According to one embodiment, the sustained release formulation provides a relatively constant level of active composition release. According to another embodiment, the sustained release formulation is contained in a device that may be actuated by the subject or medical personnel, upon onset of certain symptoms, for example, to deliver predetermined dosages of the treatment composition. The amount of the treatment composition contained within a sustained release formulation depends upon the site of implantation, the rate and expected duration of release, and the nature of the condition to be treated or prevented.

Compositions of the present invention for treatment of cortical disorders or conditions, such as seizures, seizure disorders, epilepsy, status epilepticus, migraine, spreading depression, and other conditions characterized by synchronized neuronal population activity, as well as intracranial hypertension, central nervous system edema, neurotoxicity, and the like, are preferably administered using a formulation and a route of administration that facilitates delivery of the treatment composition(s) to the central nervous system.

Treatment compositions, such as ion-dependent cotransporter antagonists, preferably cation-chloride cotransporter antagonists, may be formulated to facilitate crossing of the blood brain barrier as described above, or may be co-administered with an agent that crosses the blood brain barrier. Treatment compositions may be delivered in liposome formulations, for example, that cross the blood brain barrier, or may be co-administered with other compounds, such as bradykinins, bradykinin analogs or derivatives, or other compounds, such as SERAPORT, that cross the blood brain barrier. Alternatively, treatment compositions of the present invention may be delivered using a spinal tap that places the treatment composition directly in the circulating cerebrospinal fluid. For some treatment conditions, such as chronic epilepsy, episodic seizures, and during some episodes of spreading depression and migraine headache, there may be transient or permanent breakdowns of the blood brain barrier and specialized formulation of the treatment composition to cross the blood brain barrier may not be necessary.

Routes and frequency of administration of the therapeutic compositions disclosed herein, as well as dosages, vary according to the indication, and from individual to individual, and may be readily determined by a physician from information that is generally available and by monitoring patients and adjusting the dosages and treatment regimen accordingly using standard techniques. In general, appropriate dosages and treatment regimen provide the active composition(s) in an amount sufficient to provide therapeutic and/or prophylactic benefit. Dosages and treatment regimen may be established by monitoring improved clinical outcomes in treated patients as compared to non-treated patients. A therapeutically effective dose is an amount of a compound that, when administered as described above, produces a therapeutic response in a patient. Therapeutically effective dosages and treatment regimen will depend on the condition, the severity of the condition, and the general state of the patient being treated. Since the pharmacokinetics and pharmacodynamics of the treatment compositions of the present invention vary in different patients, a preferred method for determining a therapeutically effective dosage in a patient is to gradually escalate the dosage and monitor the clinical and laboratory indicia. For combination therapy, the two or more agents are coadministered such that each of the agents is present in a therapeutically effective amount for sufficient time to produce a therapeutic or prophylactic effect. The term "coadministration" is intended to encompass simultaneous or sequential administration of two or more agents in the same formulation or unit dosage form or in separate formulations. Appropriate dosages and treatment regimen for treatment of acute episodic conditions, chronic conditions, or prophylaxis will necessarily vary to accommodate the condition of the patient.

A pharmaceutical preparation of the present invention may be administered alone or, optionally, in combination with one or more additional treatment agents. In combination treatment for seizures and seizure-related disorders, such as epilepsy, treatment compositions of the present invention comprising an ion-dependent cotransporter antagonist, preferably a cation-chloride cotransporter antagonist, are administered in combination with one or more anti-convulsants or anti-epileptic drugs, and preferably with a BBB permeability enhancer and/or a hyperosmotic agent using a delivery system that delivers the treatment composition(s) to the central nervous system. Often the dose of the anti-convulsant or anti-epileptic drug may be less than the standard dosage as a consequence of the neurophysiological activity of the ion-dependent cotransporter antagonist. Illustrative compositions for treatment in combination with the subject compositions comprising ion-dependent antagonists, include, for example, phenytoin, carbamazepine, barbiturates, phenobarbital, pentobarbital, mephobarbital, trimethadione, mephenytoin, paramethadione, phenthenylate, phenacemide, metharbital, benzchlorpropanmide, phensuximide, primidone, methsuximide, ethotoin, aminoglutethimide, diazepam, clonazepam, clorazepate, fosphenytoin, ethosuximide, valporate, felbamate, gabapentin, lamotrigine, topiramate, vigrabatrin, tiagabine, zonisamide, clobazam, thiopental, midazoplam, propofol, levetiracetam, oxcarbazepine, CCPene, GYK152466 and sumatriptan. As can be readily appreciated, the above-noted compounds are only examples of suitable treatment combinations, and other compounds or similar classes of compounds are also suitable.

In one preferred embodiment for treating status epilepticus, a treatment composition of the present invention having ion-dependent cotransporter antagonist activity, preferably cation-chloride cotransporter activity, such as furosemide or another loop diuretic, is administered in combination with an anti-seizure agent, such as a barbiturate. Preferably, a hyperosmotic agent such as mannitol will also be administered, preferably as a bolus iv infusion into the internal carotid or vertebral artery (e.g., 0.25–1 gm/kg body weight infused over 10–30 minutes). For reducing intracranial pressure, the serum osmolality should not be greater than 320 mOsm/L serum. In this treatment regimen, the barbiturate, or another anti-seizure agent acts, via synaptic mechanisms, to damp the hyperexcitability of the neuronal population activity and to treat the symptoms of the seizure. The ion-dependent cotransporter antagonist acts, via non-synaptic mechanisms, to damp the hypersynchronization of neuronal population activity in the area of the seizure activity. This combination of treatment compositions may be administered on an emergency basis for treatment of status epilepticus and may be administered using a variety of delivery techniques that deliver the treatment compositions to the central nervous system.

The present invention thus contemplates treatment regimen involving administration of a combination of one or more ion-dependent cotransporter antagonist(s), preferably one or more cation-chloride transporter antagonists, such as furosemide, furosemide-related compounds, loog diurectics, thiazides and thiazide-related compounds, with one or more anti-seizure agent(s) selected, for example, from the following: phenytoin, carbamazepine, barbiturates, Phenobarbital, pentobarbital, mephobarbital, trimethadione, mephenytoin, paramethadione, phenthenylate, phenacemide, metharbital, benzchlorpropanmide, phensuximide, primidone, methsuximide, ethotoin, aminoglutethimide, diazepam, clonazepam, clorazepate, fosphenytoin, ethosuximide, valporate, felbamate, gabapentin, lamotrigine, topiramate, vigrabatrin, tiagabine, zonisamide, clobazam, thiopental, midazoplam, propofol, levetiracetam, oxcarbazepine, CCPene, GYK152466 and sumatriptan. The present invention also contemplates a combination comprising one or more chloride cotransporter antagonists with one or more anti-convulsant or anti-seizure agents. According to one embodiment, the combination comprises a preselected dosage of one or more anti-convulsant or anti-seizure agents sufficient to reduce hyperexcitability for a period of two hours or less, with a preselected dosage of one or more anion-dependent cotransporter antagonists sufficient to reduce hypersynchronization of neuronal population activity for a period of two hours or more. In another embodiment, the combination comprises a hyperosmotic agent, one or more cation chloride cotransporter antagonists and one or more anti-convulsant or anti-seizure agents. In yet another embodiment, the combination comprises a BBB permeability enhancer, one or more cation chloride cotransporter antagonists and one or more anti-convulsant or anti-seizure agents. In another embodiment, the combination comprises a BBB permeability enhancer, a hyperosmotic agent, one or more cation chloride cotransporter antagonists and one or more anti-convulsant or anti-seizure agents.

According to a preferred embodiment, the present invention contemplates a container having a combination of preselected dosages of furosemide, a furosemide-like composition, another loop diuretic, thiazide or a thiazide-like composition, or another ion-dependent cotransporter antagonist, with an anti-seizure or anti-convulsive agent, such as a barbiturate. The combination may also comprise a BBB permeability enhancer and/or a hyperosmotic agent. The term "container" contemplates packets, jars, vials, bottles and other containers for treatment compositions in a solid or particulate delivery system, as well as syringes and other liquid containment means, such as various types of bags, vials, bottles, and the like, having contained therein, preselected dosages of the combination agents of the present invention. The combination may be packaged and administered such that each composition of the combination is packaged and administered separately, or, the compositions may be packaged and administered as a mixture for simultaneous administration. The present invention also contemplates an emergency or surgical suite in a hospital, clinic, mobile unit, or the like, equipped with one or more containers having a combination of preselected dosages of an ion-dependent cotransporter antagonist with an anti-convulsant or anti-epileptic agent.

Treatment compositions of the present invention for treating migraine headaches, cortical spreading depression and other headache conditions comprise an ion-dependent cotransporter antagonist, preferably a cation-chloride cotransporter antagonist, optionally in combination with one or more other therapeutic compositions. The ion-dependent cotransporter antagonist may be administered either together or in conjunction with other treatment modalities, or separately, for example at different times or using different delivery techniques. Often the dose of a conventional treatment composition for migraine or spreading depression may be reduced to less than a standard dosage when the treatment is combined with administration of an ion-dependent cotransporter antagonist.

The present invention thus contemplates regimen for treating migraine headaches, cortical spreading depression and other headache conditions, and symptoms of such conditions, involving administration of a combination of one or more ion-dependent cotransporter antagonist(s) selected, for example, from one of the following: furosemide or a furosemide-related compound, other loop diuretics and loop diuretic-related compounds, thiazide and thiazide-like diuretics, including, for example, bendoroflumethiazide, benzthiazide, chlorothiazide; hydrochlorothiazide, hydroflumethiazide, methclothiazide, polythiazide, trichlormethiazide, chlorthalidone, indapamide, metolazone and quinethazone. A prophylactic or therapeutic treatment regimen may also contemplate administration of one or more ion-dependent cotransporter antagonist(s) with one or more agent(s) selected, for example, from one of the following: non-steroidal anti-inflammatory drugs, neuroleptics, corticosteroids, vasoconstrictors, beta-blockers, antidepressants, anticonvulsants, particularly Depakote, Ergot alkaloids, tryptans, Acetaminophen, caffeine, Ibuprofen, Proproxyphene, oxycodone, codeine, isometheptene, serotonin receptor agonists, ergotamine, dihydroergotamine, sumatriptan, propranolol, metoprolol, atenolol, timolol, nadolol, nifeddipine, nimodipine, verapamil, aspirin, ketoprofen, tofenamic acid, mefenamic acid, naproxen, methysergide, paracetamol, clonidine, lisuride, iprazochrome, butalbital, benzodiazepines, and divalproex sodium. As can be readily appreciated, the above-noted compounds are only examples of suitable combined treatments and other compounds or similar classes of compounds are equally suitable (e.g., combinations of the above agents with an anti-emetic and/or a nonsteroidal anti-inflammatory drug). Another embodiment of the present invention involves administration of an ion-dependent cotransporter antagonist, as described above, in combination with: one or more additional agents, as described above, with a BBB opener, or permeability enhancer, and/or a hyperosmotic agent. This combination is useful prophylactically, to prevent migraine aura from developing, and therapeutically, to reverse prolonged aura and treat migraine headache.

According to a preferred embodiment, the present invention contemplates a container having a combination of preselected dosages of furosemide, a furosemide-like composition, another loop diuretic, thiazide or a thiazide-like composition, or another ion-dependent cotransporter antagonist, as described, with another agent selected from the group consisting of: non-steroidal anti-inflammatory drugs, neuroleptics, corticosteroids, vasoconstrictors, beta-blockers, antidepressants, anticonvulsants, particularly Depakote, Ergot alkaloids, tryptans, Acetaminophen, caffeine, Ibuprofen, Proproxyphene, oxycodone, codeine, isometheptene, serotonin receptor agonists, ergotamine, dihydroergotamine, sumatriptan, propranolol, metoprolol, atenolol, timolol, nadolol, nifeddipine, nimodipine, verapamil, aspirin, ketoprofen, tofenamic acid, mefenamic acid, naproxen, methysergide, paracetamol, clonidine, lisuride, iprazochrome, butalbital, benzodiazepines, and divalproex sodium. The combination may also comprise a BBB permeability enhancer and/or a hyperosmotic agent. The term "container" contemplates packets, jars, vials, bottles and other containers for treatment compositions in a solid or particulate delivery system, as well as syringes and other liquid containment means, such as various types of bags, vials, bottles, and the like, having contained therein, preselected dosages of the combination agents of the present invention. The combination may be packaged and administered such that each composition of the combination is packaged and administered separately, or, the compositions may be packaged and administered as a mixture for simultaneous administration. The present invention also contemplates an emergency or surgical suite in a hospital, clinic, mobile unit, or the like, equipped with one or more containers having a combination of preselected dosages of an ion-dependent cotransporter antagonist with one or more of the additional agents described above.

Treatment compositions of the present invention for treating intracranial hypertension, neuropsychiatric disorders, central nervous system edema, and for treating or protecting from neurotoxicity resulting from exposure to neurotoxic agents such as ethanol, infectious agents, and the like, comprise an ion-dependent cotransporter antagonist. The treatment composition may optionally be administered in combination with one or more other therapeutic compositions. Delivery systems providing delivery of the ion-dependent cotransporter antagonist composition to the central nervous system are preferred.

Treatment compositions of the present invention for reducing pain comprise an ion-dependent cotransporter antagonist, preferably a cation-chloride cotransporter antagonist, optionally in combination with one or more other therapeutic compositions. Such treatment compositions preferably do not have the ability to cross the blood brain barrier and circulate in the peripheral nervous system only. Delivery systems providing delivery of the ion-dependent cotransporter antagonist composition to the peripheral nervous system are preferred.

Treatment compositions of the present invention for enhancing cortical function in regions such as cognitive, learning and memory centers comprise an ion-dependent cotransporter agonist, preferably a cation-chloride cotransporter agonist, optionally in combination with one or more other therapeutic compositions. Suitable delivery systems provide delivery of the ion-dependent cotransporter agonist treatment composition preferentially to the central nervous system, and more preferably to localized cortical centers of cognition, learning and/or memory.

Methods and systems of the present invention may also be used to evaluate candidate compounds and treatment regimen for diagnosis and treatment of various disorders and conditions. Various techniques for generating candidate compounds potentially having the desired ion-dependent cotransporter agonist or antagonist activity may be employed. Candidate compounds may be generated using well known combinatorial chemistry or molecular modeling techniques starting with known ion-dependent cotransporter antagonists, such as loop diuretics, including furosemide, bumetanide, ethacrinic acid, and the like, and related compounds, and modifying those compounds in ways that would be expected to confer the desired activities and specificities. Similarly, candidate chloride cotransporter agonist compounds may be generated using combinatorial chemistry techniques or molecular modeling techniques starting with known ion-dependent cotransporter agonists, and related compounds, and modifying those compounds in ways that would be expected to confer the desired activities and specificities. Methods for screening candidate compounds for desired activities are described in U.S. Pat. Nos. 5,902,732, 5,976,825, 6,096,510 and 6,319,682, which are incorporated herein by reference in the entireties.

Candidate compounds may be screened for chloride cotransporter agonist and/or antagonist activity using screening methods of the present invention with various types of cells in culture such as glial cells, neuronal cells, renal cells, and the like, or in situ in animal models. Screening techniques to identify chloride cotransporter antagonist activity, for example, may involve altering the ionic balance of the extracellular space in the tissue culture sample, or in situ in an animal model, by producing a higher than "normal" anionic chloride concentration. The geometrical and/or optical properties of the cell or tissue sample subject to this altered ionic balance are determined, and candidate agents are administered. Following administration of the candidate agents, the corresponding geometrical and/or optical properties of the cell or tissue sample are monitored to determine whether the ionic imbalance remains, or whether the cells responded by altering the ionic balances in the extracellular and intracellular space. If the ionic imbalance remains, the candidate agent is likely a chloride cotransporter antagonist. By screening using various types of cells or tissues, candidate compounds having a high level of glial cell chloride cotransporter antagonist activity and having a reduced level of neuronal cell and renal cell chloride cotransporter antagonist activity may be identified. Similarly, effects on different types of cells and tissue systems may be assessed.

Additionally, the efficacy of candidate compounds for treating various conditions of the central and peripheral nervous system may be assessed by simulating or inducing a condition, such as a seizure, central nervous system edema, ethanol neurotoxicity, cortical spreading depression, or the like, in a tissue sample or in situ in an animal model, monitoring the geometrical and/or optical properties of the cell or tissue sample during stimulation of the condition, administering the candidate compound, then monitoring the geometrical and/or optical properties of the cell or tissue sample following administration of the candidate compound, and comparing the geometrical and/or optical properties of the cell or tissue sample to determine the effect of the candidate compound. Similarly, the efficacy of treatment composition(s) in an animal or human subject may be monitored in situ using the optical methods and systems of the present invention.

The treatment compositions and methods of the present invention have been described, above, with respect to certain preferred embodiments. The Examples set forth below describe the results of specific experiments and are not intended to limit the invention in any fashion.

EXAMPLE 1

The Effects of Furosemide on Epileptiform Discharges in Hippocampal Slices

During these studies, spontaneous epileptiform activity was elicited by a variety of treatments. Sprague-Dawley rats (males and females; 25–35 days old) were decapitated, the top of the skull was rapidly removed, and the brain chilled with ice-cold oxygenated slicing medium. The slicing medium was a sucrose-based artificial cerebrospinal fluid (sACSF) consisting of 220 mM sucrose, 3 mM KCl, 1.25 mM $NaH_2PO_4$, 2 mM $MgSO_4$, 26 mM $NaHCO_3$, 2 mM $CaCl_2$, and 10 mM dextrose (295–305 mOsm). A hemisphere of brain containing hippocampus was blocked and glued (cyanoacrylic adhesive) to the stage of a Vibroslicer (Frederick Haer, Brunsick, Me.). Horizontal or transverse slices 400 μm thick were cut in 4° C., oxygenated (95% $O_2$; 5% $CO_2$) slicing medium. The slices were immediately transferred to a holding chamber where they remained submerged in oxygenated bathing medium (ACSF) consisting of 124 mM NaCl, 3 mM KCl, 1.25 mM $NaH_2PO_4$, 2 mM $MgSO_4$, 26 mM $NaHCO_3$, 2 mM $CaCl_2$, and 10 mM dextrose (295–305 mOsm). The slice were held at room temperature for at least 45 minutes before being transferred to submersion-style recording chamber (all other experiments). In the recording chamber, the slices were perfused with oxygenated recording medium at 34–35° C. All animal procedures were conducted in accordance with NIH and University of Washington animal care guidelines.

In most slice experiments, simultaneous extracellular field electrode recordings were obtained from CA1 and CA3 areas. A bipolar tungsten stimulating electrode was placed on the Schaffer collaterals to evoke synaptically-driven field responses in CA1. Stimuli consisted of 100–300 □sec duration pulses at an intensity of four times the population-spike threshold. After discharges were evoked by a 2 second train of such stimuli delivered at 60 Hz. Spontaneous interictal-like bursts were observed in slices treated by the following modifications or additions to the bathing medium:

10 mM potassium (6 slices; 4 animals; average—81 bursts/min.); 200–300 □M 4-aminopyridine (4 slices; 2 animals; average—33 burst/min.); 50–100 □M bicuculline (4 slices; 3 animals; average—14 bursts/min); ) M $Mg^{++}$ (1 hour of perfusion—3 slices; 2 animals; average—20 bursts/min. or 3 hours of perfusion—2 slices; 2 animals); zero calcium/6 mM KCl and 2 mM EGTA (4 slices; 3 animals). In all treatments, furosemide was added to the recording medium once a consistent level of bursting was established.

In the first of these procedures, episodes of after discharges were evoked by electrical stimulation of the Schaffer collaterals (Stasheff et al., Brain Res. 344:296, 1985) and the extracellular field response was monitored in the CA1 pyramidal cell region (13 slices; 8 animals). The concentration of $Mg^{++}$ in the bathing medium was reduced to 0.9 mM and after discharges were evoked by stimulation at 60 Hz for 2 seconds at an intensity 4 times the population spike threshold (population spike threshold intensity varied between 20–150 μA at 100–300 μsec pulse duration). The tissue was allowed to recover for 10 minutes between stimulation trials. In each experiment, the initial response of CA1 to synaptic input was first tested by recording the field potential evoked by a single stimulus pulse. In the control condition, Schaffer collateral stimulation evoked a single population spike (FIG. 1A, inset). Tetanic stimulation evoked approximately 30 seconds after discharge (FIG. 1A, left) associated with a large change in intrinsic signal (FIG. 1A, right).

For imaging of intrinsic optical signals, the tissue was placed in a perfusion chamber located on the stage of an upright microscope and illuminated with a beam of white light (tungsten filament light and lens system—Dedo Inc.) directed through the microscope condenser. The light was controlled and regulated (power supply—Lamda Inc.) to minimize fluctuations and filtered (695 nm longpass) so that the slice was transilluminated with long wavelengths (red). Field of view and magnification were determined by the choice of microscope objectives (4× for monitoring the entire slice). Image-frames were acquired with a charge-coupled device (CCD) camera (Dage MTI Inc.) at 30 HZ and were digitized at 8 bits with a spatial resolution of 512×480 pixels using an Imaging Technology Inc. Series 151 imaging system; gains and offsets of the camera-control box and the A/D board were adjusted to optimize the sensitivity of the system. Imaging hardware was controlled by a 486-PC compatible computer. To increase signal/noise, an averaged-image was composed from 16 individual image-frames, integrated over 0.5 sec and averaged together. An experimental series typically involved the continuous acquisition of a series of averaged-images over a several minute time period; at least 10 of these averaged-images were acquired as control-images prior o stimulation. Pseudocoloured images were calculated by subtracting the first control-image from subsequently acquired images and assigning a color lookup table to the pixel values. For these images, usually a linear low-pass filter was used to remove high frequency noise and a linear-histogram stretch was used to map the pixel values over the dynamic range of the system. All operations on these images were linear so that quantitative information was preserved. Noise was defined as the maximum standard deviation of fluctuations of $\Delta R/R$ of the sequence of control images within a given acquisition series, where $\Delta R/R$ represented the magnitude of the change in light-transmission through the tissue. Delta R/R was calculated by taking all the difference-images and dividing by the first control image: (subsequent image—first-control-image)/first-control-image. The noise was always <0.01 for each of the chosen image sequences. The absolute change in light transmission through the tissue was estimated during some experiments by acquiring images after placing neutral density filters between the camera and the light source. On average, the camera electronics and imaging system electronics amplified the signal 10-fold prior to digitization so that the peak absolute changes in light transmission through the tissue were usually between 1% and 2%.

Figure 1D:
Figure 1D:
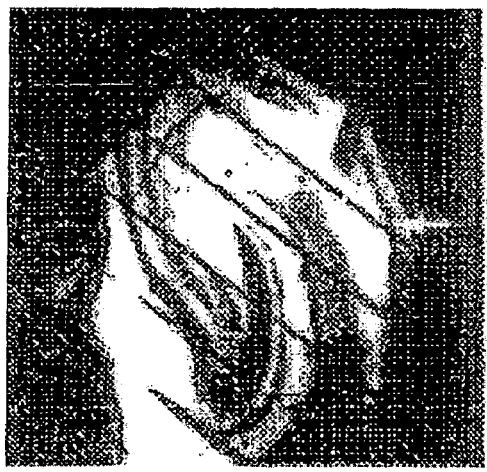

The gray-scale photo shown in FIG. 1D is a video image of a typical hippocampal slice in the recording chamber. The fine gold-wire mesh that was used to hold the tissue in place can be seen as dark lines running diagonally across the slice. A stimulating electrode can be seen in the upper right on the stratum radiatum of CA1. The recording electrode (too thin to be seen in the photo) was inserted at the point indicated by the white arrow. FIG. 1A illustrates that two seconds of stimulation at 60 Hz elicited after discharge activity and shows a typical after discharge episode recorded by the extracellular electrode. The inset of FIG. 1A shows the CA1 field response to a single 200 sec test pulse (artifact at arrow) delivered to the Schaffer collaterals. FIG. 1A1 shows a map of the peak change in optical transmission through the tissue evoked by Schaffer collateral stimulation. The region of maximum optical change corresponds to the apical and basal dendritic regions of CA1 on either side of the stimulating electrode. FIG. 1B illustrates sample traces showing responses to stimulation after 20 minutes of perfusion with medium containing 2.5 mM furosemide. Both the electrical after discharge activity (shown in FIG. 1B) and the stimulation-evoked optical changes (shown in FIG. 1B1) were blocked. However, there was a hyper-excitable field response (multiple population spikes) to the test pulse (inset). FIGS. 1C and 1C1 illustrate that restoration of initial response patterns was seen after 45 minutes of perfusion with normal bathing medium.

The opposing effects of furosemide-blockade of the stimulation-evoked after discharges and a concomitant increase of the synaptic response to a test-pulse illustrate the two key results: (1) furosemide blocked epileptiform activity, and (2) synchronization (as reflected by spontaneous epileptiform activity) and excitability (as reflected by the response to a single synaptic input) were dissociated. Experiments in which the dose-dependency of furosemide was examined determined that a minimum concentration of 1.25 mM was required to block both the after discharges and optical changes.

EXAMPLE 2

Figure 2A:
FIGS. 2A–2R show furosemide blockade of spontaneous epileptiform burst discharges across a spectrum of in vitro models.
Figure 2B:
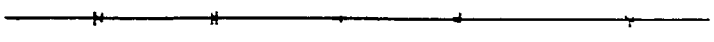
Figure 2C:
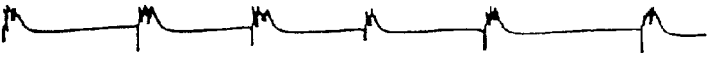
Figure 2D:
Figure 2E:
Figure 2F:
Figure 2G:
Figure 2H:
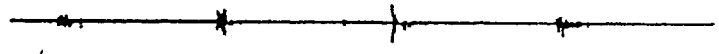

The Effects of Furosemide on Epileptiform Discharges in Hippocampal Slices Perfused with High-$K^+$ (10 mM) Bathing Medium Rat hippocampal slices, prepared as described above, were perfused with a high-$K^+$ solution until extended periods of spontaneous interictal-like bursting were recorded simultaneously in CA3 (top traces) and CA1 (lower traces) pyramidal cell regions (FIGS. 2A and 2B). After 15 minutes of perfusion with furosemide-containing medium (2.5 mM furosemide), the burst discharges increased in magnitude (FIGS. 2C and 2D). However, after 45 minutes of furosemide perfusion, the bursts were blocked in a reversible manner (FIGS. 2E, 2F, 2G and 2H). During this entire sequence of furosemide perfusion, the synaptic response to a single test pulse delivered to the Schaffer colaterals was either unchanged or enhanced (data not shown). It is possible that the initial increase in discharge amplitude reflected a furosemide-induced decrease in inhibition (Misgeld et al., *Science* 232:1413, 1986; Thompson et al., *J. Neurophysiol.* 60:105, 1988; Thompson and Gähwiler, *J. Neuropysiol.* 61:512, 1989; and Pearce, *Neuron* 10:189, 1993). It has previously been reported (Pearce, *Neuron* 10:189, 1993) that furosemide blocks a component of the inhibitory currents in hippocampal slices with a latency (<15 min.) similar to the time to onset of the increased excitability observed here. The longer latency required for the furosemide-block of the spontaneous bursting might correspond to additional time required for a sufficient block of the furosemide-sensitive cellular volume regulation mechanisms under high-$K^+$ conditions.

Figure 2I:
Figure 2J:
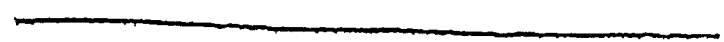
Figure 2K:
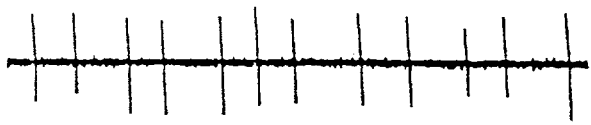
Figure 2L:
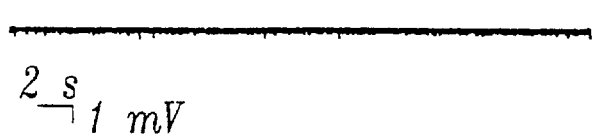
Figure 2M:
Figure 2N:
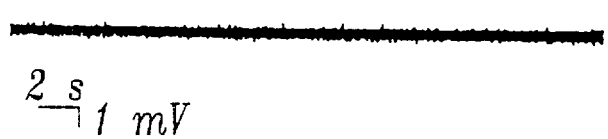
Figure 2O:
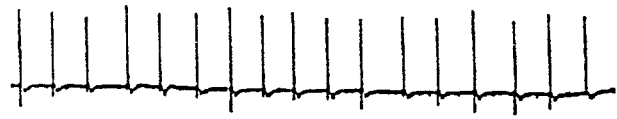
Figure 2P:
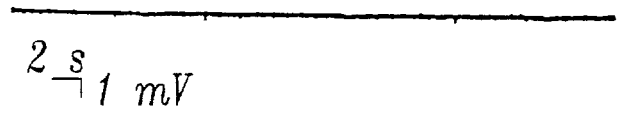
Figure 2Q:
Figure 2R:

After testing the effects of furosemide on slices perfused with high-$K^+$, similar studies were performed with a variety of other commonly studied in vitro models of epileptiform discharge (Galvan et al., *Brain Res.* 241:75, 1982; Schwartzkroin and Prince, *Brain Res.* 183:61, 1980; Anderson et al., *Brain Res.* 398:215, 1986; and Zhang et al., *Epilepsy Res.* 20:105, 1995). After prolonged exposure (2–3 hours) to magnesium-free medium (0-$Mg^{++}$), slices have been shown to develop epileptiform discharges that are resistant to common clinically used anticonvulsant drugs (Zhang et al., *Epilepsy Res.* 20:105, 1995). Recordings from entorhinal cortex (FIG. 2I) and subiculum (not shown) showed that after 3 hours of perfusion with 0-$Mg^{++}$ medium, slices developed bursting patterns that appeared similar to these previously described "anticonvulsant resistant" bursts. One hour after the addition of furosemide to the bathing medium, these bursts were blocked (FIG. 2J). Furosemide also blocked spontaneous burst discharges observed with the following additions/modifications to the bathing medium: (1) addition of 200–300 μM 4-aminopyridine (4-AP; a potassium channel blocker) (FIGS. 2K and 2L); (2) addition of the GABA antagonist, bicuculline, at 50–100 μM (FIGS. 2M ad 2N); (3) removal of magnesium (0-$Mg^{++}$)—1 hours perfusion (FIGS. 2O and 2P); and (4) removal of calcium plus extracellular chelation (0-$Ca^{++}$) (FIGS. 2Q and 2R). With each of these manipulations, spontaneous interictal-like patterns were simultaneously recorded from CA1 and CA3 subfields (FIGS. 2K, 2L, 2M and 2N show only the CA3 trace and FIGS. 2O, 2P, 2Q, and 2R show only the CA1 trace). In the 0-$Ca^{++}$ experiments, 5 mM furosemide blocked the bursting with a latency of 15–20 minutes. For all other protocols, bursting was blocked by 2.5 mM furosemide with a latency of 20–60 minutes. Furosemide reversibly blocked the spontaneous bursting activity in both CA1 and CA3 in all experiments (FIGS. 2L, 2N, 2P and 2R).

EXAMPLE 3

The Effects of Furosemide on Epileptiform Activity Induced by i.v. Injection of Kainic Acid in Anesthetized Rats This example illustrates an in vitro model in which epileptiform activity was induced by i.v. injection of kainic acid (KA) into anesthetized rats (Lothman et al., *Neurology* 31:806, 1981). The results are illustrated in FIGS. 3A–3H. Sprague-Dawley rats (4 animals; weights 250–270 g) were anesthetized with urethane (1.25 g/kg i.p.) and anesthesia maintained by additional urethane injections (0.25 g/kg i.p.) as needed. Body temperature was monitored using a rectal temperature probe and maintained at 35–37° C. with a heating pad; heart rate (EKG) was continuously monitored. The jugular vein was cannulated on one side for intravenous drug administration. Rats were placed in a Kopf stereotaxic device (with the top of the skull level), and a bipolar stainless-steel microelectrode insulated to 0.5 mm of the tip was inserted to a depth of 0.5–1.2 mm from the cortical surface to record electroencephalographic (EEG) activity in the fronto-parietal cortex. In some experiments, a 2M NaCl-containing pipette was lowered to a depth of 2.5–3.0 mm to record hippocampal EEG. Data were stored on VHS video-tape and analyzed off-line.

Following the surgical preparation and electrode placement, animals were allowed to recover for 30 minutes before the experiments were initiated with an injection of kainic acid (10–12 mg/kg i.v.). Intense seizure activity, an increased heart rate, and rapid movements of the vibrissae were induced with a latency of about 30 minutes. Once stable electrical seizure was evident, furosemide was delivered in 20 mg/kg boluses every 30 minutes to a total of 3 injections. Experiments were terminated with the intravenous administration of urethane. Animal care was in accordance with NIH guidelines and approved by the University of Washington Animal Care Committee.

FIGS. 3A–3H show furosemide blockade of kainic acid-evoked electrical "status epilepticus" in urethane-anesthetized rats. EKG recordings are shown as the top traces and EEG recordings are shown as the bottom traces. In this model, intense electrical discharge (electrical "status epilepticus") was recorded from the cortex (or from depth hippocampal electrodes) 30–60 minutes after KA injection (10–12 mg/kg) (FIGS. 3C and 3D). Control experiments (and previous reports, Lothman et al., *Neurology,* 31:806, 1981) showed that this status-like activity was maintained for well over 3 hours. Subsequent intravenous injections of furosemide (cumulative dose: 40–60 mg/kg) blocked seizure activity with a latency of 30–45 minutes, often producing a relatively flat EEG (FIGS. 3E, 3F, 3G and 3H). Even 90 minutes after the furosemide injection, cortical activity remained near normal baseline levels (i.e., that observed prior to the KA and furosemide injections). Studies on the pharmacokinetics of furosemide in the rat indicate that the dosages used in this example were well below toxic levels (Hammarlund and Paalzow, *Biopharmaceutics Drug Disposition,* 3:345, 1982).

EXPERIMENTAL METHODS FOR EXAMPLES 4–7

Hippocampal slices were prepared from Sprague-Dawley adult rats as described previously. Transverse hippocampal slices 100 μm thick were cut with a vibrating cutter. Slices typically contained the entire hippocampus and subiculum. After cutting, slices were stored in an oxygenated holding chamber at room temperature for at least one hour before recording. All recordings were acquired in an interface type chamber with oxygenated (95% $O_2$, 5% $CO_2$) artificial cerebral spinal fluid (ACSF) at 34°–35° C. Normal ACSF contained (in mmol/l): 124 NaCl, 3 KCl, 1.25 $NaH_2PO_4$, 1.2 $MgSO_4$, 26 $NaHCO_3$, 2 $CaCl_2$, and 10 dextrose.

Sharp-electrodes for intracellular recordings from CA1 and CA3 pyramidal cells were filled with 4 M potassium acetate. Field recordings from the CA1 and CA3 cell body layers were acquired with low-resistance glass electrodes filled with 2 M NaCl. For stimulation of the Schaffer collateral or hilar pathways, a small monopolar tungsten electrode was placed on the surface of the slice. Spontaneous and stimulation-evoked activities from field and intracellular recordings were digitized (Neurocorder, Neurodata Instruments, New York, N.Y.) and stored on videotape. AxoScope software (Axon Instruments) on a personal computer was used for off-line analysis of data.

In some experiments, normal or low-chloride medium was used containing bicuculline (20 μM), 4-amino pyridine (4-AP) (100 μM), or high-$K^+$ (7.5 or 12 mM). In all experiments, low-chloride solutions (7, and 21 mM $[Cl^-]_o$) were prepared by equimolar replacement of NaCl with $Na^+$-gluconate (Sigma). All solutions were prepared so that they had a pH of approximately 7.4 and an osmolarity of 290–300 mOsm at 35° C. and at equilibrium from carboxygenation with 95% $O_2$/5% $CO_2$.

After placement in the interface chamber, slices were superfused at approximately 1 m/min. At this flow-rate, it took 8–10 minutes for changes in the perfusion media to be completed. All of the times reported here have taken this delay into account and have an error of approximately ±2 minutes.

EXAMPLE 4

Timing of Cessation of Spontaneous Epileptiform Bursting in Areas in CA1 and CA3

The relative contributions of the factors that modulate synchronized activity vary between areas CA1 and CA3. These factors include differences in the local circuitry and region-specific differences in cell packing and volume fraction of the extracellular spaces. If the anti-epileptic effects of anion or chloride-cotransport antagonism are due to a desynchronization in the timing of neuronal discharge, chloride-cotransport blockade might be expected to differentially affect areas CA1 and CA3. To test this, a series of experiments was performed to characterize differences in the timing of the blockade of spontaneous epileptiform activity in areas CA1 and CA3.

Field activity was recorded simultaneously in areas CA1 and CA3 (approximately midway between the most proximal and distal extent the CA3 region), and spontaneous bursting was induced by treatment with high-$[K^+]_o$ (12 μM; n=12), bicuculline (20 mM; n=12), or 4-AP (100 μM; n=5). Single electrical stimuli were delivered to the Schaffer collaterals, midway between areas CA1 and CA3, every 30 seconds so that the field responses in areas CA1 and CA3 could be monitored throughout the duration of each experiment. In all experiments, at least 20 minutes of continuous spontaneous epileptiform bursting was observed prior to switching to low $[Cl^-]_o$ (21 mM) or furosemide-containing (2.5 mM) medium.

In all cases, after 30–40 minutes exposure to furosemide or low-chloride medium, spontaneous bursting ceased in area CA1 before the bursting ceased in area CA3. The temporal sequence of events typically observed included an initial increase in burst frequency and amplitude of the spontaneous field events, then a reduction in the amplitude of the burst discharges which was more rapid in CA1 than in CA3. After CA1 became silent, CA3 continued to discharge for 5–10 minutes, until it too no longer exhibited spontaneous epileptiform events.

This temporal pattern of burst cessation was observed with all epileptiform-inducing treatments tested, regardless of whether the agent used for blockade of spontaneous bursting was furosemide or low-$[Cl^-]_o$ medium. Throughout all stages of these experiments, stimulation of the Schaffer collaterals evoked hyperexcited field responses in both the CA1 and CA3 cell body layers. Immediately after spontaneous bursting was blocked in both areas CA1 and CA3, hyperexcited population spikes could still be evoked.

We considered the possibility that the observed cessation of bursting in CA1 prior to CA3 was an artifact of the organization of synaptic contacts between these areas relative to our choice of recording sites. It is known that the projections of the various subregions of CA3 terminate in an organized fashion in CA1; CA3 cells closer to the dentate gyrus (proximal CA3) tend to project most heavily to the distal portions of CA1 (near the subicular border), whereas CA3 projections arising from cells located more distally in CA3 terminate more heavily in portions of CA1 located closer to the CA2 border. If the cessation of bursting occurs in the different subregions of CA3 at different times, the results of the above set of experiments might arise not as a difference between CA1 and CA3, but rather as a function of variability in bursting activity across CA3 subregions. We tested this possibility in three experiments. Immediately after the spontaneous bursting ceased in CA1, we surveyed the CA3 field with a recording electrode. Recordings form several different CA3 locations (from the most proximal to the most distal portions of CA3), showed that all subregions of area CA3 were spontaneously bursting during this time that CA1 was silent.

The observation that CA3 continued to discharge spontaneously after CA1 became silent was unexpected since population discharges in CA3 are generally thought to evoke discharges in CA1 through excitatory synaptic transmission. As previously described, single-pulse stimuli delivered to the Schaffer collaterals still evoked multiple population spikes in CA1 even after the blockade of spontaneous bursting; thus, hyperexcited excitatory synaptic transmissions in CA3-to-CA1 synapse was intact. Given this maintained efficacy of synaptic transmission, and the continued spontaneous field discharges in CA3, we postulated that the loss of spontaneous bursting in CA1 was due to a decrease in synchronization of incoming excitatory drive. Further, since spontaneous epileptiform discharge in CA3 also eventually ceased, perhaps this desynchronization process occurred at different times in the two hippocampal subfields.

EXAMPLE 5

Effect of Chloride-Cotransport Antagonism on the Synchronization of CA1 and CA3 Field Population Discharges The observation from Example 4 suggested a temporal relationship between the exposure time to low-$[Cl^-]_o$ or furosemide-containing medium and the characteristics of the spontaneous burst activity. Further, this relationship was different between areas CA1 and CA3. In order to better characterize the temporal relationships, we compared the occurrences of CA1 action potentials and the population spike events in the field responses of CA1 and CA3 subfields during spontaneous and stimulation-evoked burst discharge.

Intracellular recordings were obtained from CA1 pyramidal cells, with the intracellular electrode placed close (<100 μM) to the CA1 field electrode. The slice was stimulated every 20 seconds with single stimuli delivered to the Schaffer collaterals. After continuous spontaneous bursting was established for at least 20 minutes, the bathing medium was switched to bicuculline-containing low-$[Cl^-]_o$ (21 mM) medium. After approximately 20 minutes, the burst frequency and amplitude was at its greatest. Simultaneous field and intracellular recordings during this time showed that the CA1 field and intracellular recordings were closely synchronized with the CA3 field discharges. During each spontaneous discharge, the CA3 field response preceded the CA1 discharge by several milliseconds. During stimulation-evoked events, action potential discharges of the CA1 pyramidal cell were closely synchronized to both CA3 and CA1 field discharges.

With continued exposure to low-$[Cl^-]_o$ medium, the latency between the spontaneous discharges of areas CA1 and CA3 increased, with a maximum latency of 30-40 milliseconds occurring after 30–40 minutes exposure to the bicuculline-containing low-chloride medium. During this time, the amplitude of both the CA1 and CA3 spontaneous field discharges decreased. Stimulation-evoked discharges during this time closely mimicked the spontaneously occurring discharges in morphology and relative latency. However, the initial stimulus-evoked depolarization of the neuron (presumably, the monosynaptic EPSP) began without any significant increase in latency. The time interval during which these data were acquired corresponds to the time immediately prior to the cessation of spontaneous bursting in CA1.

After 40–50 minutes perfusion with low-$[Cl^-]_o$ medium, the spontaneous bursts were nearly abolished in CA1 but were unaffected in CA3. Schaffer collateral stimulation during this time showed that monosynaptically-triggered responses of CA1 pyramidal cells occurred without any significant increase in latency, but that stimulation-evoked field responses were almost abolished. The time interval during which these data were acquired corresponds to the moments immediately prior to the cessation of spontaneous bursting in CA3.

After prolonged exposure to low-$[Cl^-]_o$ medium, large increases (>30 milliseconds) developed in the latency between Schaffer collateral stimulation and the consequent CA3 field discharge. Eventually, no field responses could be evoked by Schaffer collateral stimulation in either areas CA1 and CA3. However, action potential discharge from CA1 pyramidal cells in response to Schaffer collateral stimulation could be evoked with little change in response latency. Indeed, for the entire duration of the experiments (greater than two hours), action potential discharges form CA1 pyramidal cells could be evoked at short latency by Schaffer collateral stimulation. Further, although stimulation-evoked hyperexcited discharges of CA3 were eventually blocked after prolonged exposure to low-$[Cl^-]_o$ medium, the antidromic response in CA3 appeared to be preserved.

EXAMPLE 6

Effects of Chloride-Cotransport Antagonism on the Synchronization of Burst Discharges in CA1 Pyramidal Cells The foregoing data suggest the disappearance of the field responses may be due to a desynchronization of the occurrence of action potentials among neurons. That is, although synaptically-driven excitation of CA1 pyramidal cells was not preserved, action potential synchrony among the CA1 neuronal population was not sufficient to summate into a measurable DC field response. In order to test this, paired intracellular recordings of CA1 pyramidal cells were acquired simultaneously with CA1 field responses. In these experiments, both the intracellular electrodes and the field recording electrodes were placed within 200 μm of one another.

During the period of maximum spontaneous activity induced by bicuculline-containing low-$[Cl^-]_o$ medium, recordings showed that action potentials between pairs of CA1 neurons and the CA1 field discharges were tightly synchronized both during spontaneous and stimulation-evoked discharges. After continued exposure to low-$[Cl^-]_o$ medium, when the amplitude of the CA1 field discharge began to broaden and diminish, both spontaneous and stimulation-evoked discharges showed a desynchronization in the timing of the occurrences of action potentials between pairs of CA1 neurons, and between the action potentials and the field responses. This desynchronization was coincident with the suppression of CA1 field amplitude. By the time that spontaneous bursting in CA1 ceased, a significant increase in latency had developed between Schaffer collateral stimulation and CA1 field discharge. At this time, paired intracellular recordings showed a dramatic desynchronization in the timing of action potential discharge between pairs of neurons and between the occurrence of action potentials and the field discharges evoked by Schaffer collateral stimulation.

It is possible that the observed desynchronization of CA1 action potential discharge is due to the randomization of mechanisms necessary for synaptically-driven action potential generation, such as a disruption in the timing of synaptic release or random conduction failures at neuronal processes. If this were the case, then one would expect that the occurrence of action potentials between a given pair of neurons would vary randomly with respect to one another, from stimulation to stimulation. We tested this by comparing the patterns of action potential discharge of pairs of neurons between multiple consecutive stimuli of the Schaffer collaterals. During each stimulation event, the action potentials occurred at nearly identical times with respect to one another, and showed an almost identical burst morphology from stimulation to stimulation. We also checked to see whether the occurrence of action potentials between a given pair of neurons during spontaneous field discharges was fixed in time. The patterns of action potential discharges from a given pair of CA1 neurons was compared between consecutive spontaneous field bursts during the time when the occurrence of action potentials was clearly desynchronized. Just as in the case of stimulation-evoked action potential discharge described above, the action potentials generated during a spontaneous population discharge occurred at nearly identical times with respect to one another, and showed a nearly identical burst morphology from one spontaneous discharge to the next.

EXAMPLE 7

Effects if Low-Chloride Treatment on Spontaneous Synaptic Activity

It is possible that the anti-epileptic effects associated with chloride-cotransport antagonism are mediated by some action on transmitter release. Blockade of chloride-cotransport could alter the amount or timing of transmitter released from terminals, thus affecting neuronal synchronization. To test whether low-$[Cl^-]_o$ exposure affected mechanisms associated with transmitter release, intracellular CA1 responses were recorded simultaneously with CA1 and CA3 field responses during a treatment which dramatically increases spontaneous synaptic release of transmitter from presynaptic terminals.

Increased spontaneous release of transmitter was induced by treatment with 4-AP (100 μM). After 40 minutes exposure to 4-AP-containing medium, spontaneous synchronized burst discharges were recorded in area CA1 and CA3.

Switching to 4-AP-containing low-$[Cl^-]_o$ medium led initially, as was shown previously, to enhanced spontaneous bursting. High-grain intracellular recordings showed that high-amplitude spontaneous synaptic activity was elicited by 4-AP treatment. Further exposure to low-chloride medium blocked spontaneous burst discharge in CA1, although CA3 continued to discharge spontaneously. At this time, CA1 intracellular recordings showed that spontaneous synaptic noise was further increased, and remained so for prolonged exposure times to 4-AP-containing low-chloride medium. These data suggest that mechanisms responsible for synaptic release from terminals are not adversely affected by low-chloride exposure in a manner that could explain the blockade of 4-AP-induced spontaneous bursting in CA1. These results also eliminate the possibility that the effects of low-$[Cl^-]_o$ exposure are due to alterations in CA1 dendritic properties which would compromise their efficiency in conducting PSPs to the soma.

EXPERIMENTAL METHODS FOR EXAMPLES 8 to 12

In all of the following experiments, $[Cl^-]_o$ was reduced by equimolar replacement of NaCl with $Na^+$-gluconate. Gluconate was used rather than other anion replacements for several reasons. First, patch-clamp studies have demonstrated that gluconate appears to be virtually impermeant to chloride channels, whereas other anions (including methylsulfate, sulfate, isethionate, and acetate) are permeable to varying degrees. Second, transport of extracellular potassium through glial $Na^+$, $K^+$, 2Cl cotransport is blocked when extracellular chloride is replaced by gluconate but is not completely blocked when replaced by isethionate. Since this furosemide-sensitive cotransporter plays a significant role in cell swelling and volume changes of the extracellular space (ECS), we wished to use the appropriate anion replacement so that the effects of our treatment would be comparable to previous furosemide experiments. [Hochman, D. W., Baraban, S. C., Owens, J. W. M., and Schwartzkroin, P. A., "Dissociation of synchronization and excitability in furosemide blockade of epileptiform activity." Science, Vol. 270, pp. 99–102 (1995), U.S. Pat. No. 5,902,732] Third, formate, acetate, and proprionate generate weak acids when employed as $Cl^-$ substitutes and lead to a prompt fall in intracellular pH; gluconate remains extracellular and has not been reported to induce intracellular pH shifts. Fourth, for purposes of comparison we wished to use the same anion replacement that had been used in previous studies examining the effects of low-$[Cl^-]_o$ on activity-evoked changes of the ECS.

There is some suggestion that certain anion-replacements might chelate calcium. Although subsequent work has failed to demonstrate any significant ability of anion-substitutes to chelate calcium, there is still some concern in the literature regarding this issue. Calcium chelation did not appear to be an issue in the following experiments, since resting membrane potentials remained normal and synaptic responses (indeed, hyperexcitable synaptic responses) could be elicited even after several hours of exposure to medium in which $[Cl-]_o$ had been reduced by gluconate substitution. Further, we confirmed that calcium concentration in our low-$[Cl^-]_o$-medium was identical to that in our control-medium by measurements made with $Ca^{2++}$—selective microelectrodes.

Sprague-Dawley adult rats were prepared as previously described. Briefly, transverse hippocampal slices, 400 μm thick, were cut using a vibrating cutter. Slices typically contained the entire hippocampus and subiculum. After cutting, slices were stored in an oxygenated holding chamber for at least one hour prior to recording. All recordings were acquired in an interface type chamber with oxygenated (95% O2/5% CO2) artificial cerebral spinal fluid (ACSF) at 34°–35° C. Normal ACSF contained (in mmol/l): 124 NaCl, 3 KCl, 1.25 NaH2PO4, 1.2 MgSO4, 26 NaHCO3, 2 CaCl2, and 10 dextrose. In some experiments, normal or low-chloride medium was used containing bicuculline (20 μM), 4-AP (100 μM), or high-$K^+$ (12 mM). Low-chloride solutions (7, 16, and 21 mM $[Cl^-]_o$) were prepared by equimolar replacement of NaCl with $Na^+$-gluconate (Sigma Chemical Co., St. Louis, Mo.). All solutions were prepared so that they had a pH of approximately 7.4 and an osmolarity of 290–300 mOsm at 35° C. and at equilibrium from carboxygenation with 95% O2/5% CO2.

Sharp-electrodes filled with 4 M potassium acetate were used for intracellular recordings from CA1 pyramidal cells. Field recordings from the CA1 or CA3 cell body layers were acquired with low-resistance glass electrodes filled with NaCl (2 M). For stimulation of the Schaffer collateral pathway, a small monopolar electrode was placed on the surface of the slice midway between areas CA1 and CA3. Spontaneous and stimulation-evoked activities from field and intracellular recordings were digitized (Neurocorder, Neurodata Instruments, New York, N.Y.), and stored on video tape. AxoScope software (Axon Instruments Inc.) on a PC-computer was used for off-line analyses of data.

Ion-selective microelectrodes were fabricated according to standard methods well known in the art. Double-barreled pipettes were pulled and broken to a tip diameter of approximately 3.0 μm. The reference barrel was filled with ACSF and the other barrel was sylanized and the tip back-filled with a resin selective for $K^+$ (Corning 477317). The remainder of the sylanized barrel was filled with KCl (140 mM). Each barrel was led, via Ag/AgCl wires, to a high impedance dual-differential amplifier (WPI FD223). Each ion-selective microelectrode was calibrated by the use of solutions of known ionic composition and was considered suitable if it was characterized by a near-Nernstian slope response and if it remained stable throughout the duration of the experiment.

After placement in the interface chamber, slices were superfused at approximately 1 ml/minute. At this flow-rate, it took approximately 8–10 minutes for changes in perfusion media to be completed. All of the times reported here have taken this time-delay into account and have an error of approximately ±2 minutes.

EXAMPLE 8

Effects of Low-$[Cl-]_o$ on CA1 Field Recordings

Other studies have shown that prolonged exposure of cortical and hippocampal slices to low-$[Cl^-]_o$ does not affect basic intrinsic and synaptic properties such as input resistance, resting membrane potential, depolarization-induced action-potential generation, or excitatory synaptic transmission. A previous study has also partly characterized the epileptogenic properties of low-$[Cl^-]_o$ exposure to CA1 area of hippocampus. The following studies were performed to observe the times of onset and possible cessation of low-$[Cl^-]_o$-induced hyperexcitability and hypersynchronization. Slices (n=6) were initially perfused with normal medium until stable intracellular and field recordings were established in a CA1 pyramidal cell and the CA1 cell body layer, respectively. In two experiments, the same cell was held throughout the entire length of the experiment (greater than 2 hours). In the remaining experiments (n=4), the initial intracellular recording was lost during the sequence of medium changes and additional recordings were acquired from different cells. Patterns of neuronal activity in these experiments were identical to those seen when a single cell was observed.

The field and intracellular electrodes were always placed in close proximity to one another (<200 μm). In each case, after approximately 15–20 minutes exposure to the low-$[Cl^-]_o$-medium (7 mM), spontaneous bursting developed, first at the cellular level, and then in the field. This spontaneous field activity, representing synchronized burst discharge in a large population of neurons, lasted from 5–10 minutes, after which time the field recording became silent. When the field first became silent, the cell continued to discharge spontaneously. This result suggests that population activity has been "desynchronized" while the ability of individual cells to discharge has not been impaired. After approximately 30 minutes exposure to low-$[Cl^-]_o$-medium, intracellular recording showed that cells continued to discharge spontaneously even though the field remained silent. The response of the cell to intracellular current injection at two time points demonstrated that the cell's ability to generate action potentials had not been impaired by low-$[Cl-]_o$ exposure. Further, electrical stimulation in CA1 stratum radiatum elicited burst discharges, indicating that a hyperexcitable state was maintained in the tissue.

EXAMPLE 9

Effects of Low-$[Cl-]_o$ on High-$[K+]_o$-Induced Epileptiform Activity in CA1

The previous set of experiments showed that tissue exposure to low-$[Cl^-]_o$ medium induced a brief period of spontaneous field potential bursting which ceased within 10 minutes. If a reduction of $[Cl^-]_o$ is indeed eventually capable of blocking spontaneous epileptiform (i.e. synchronized) bursting, then these results suggest that antiepileptic effects would likely be observable only after this initial period of bursting activity has ceased. We therefore examined the temporal effects of low-$[Cl^-]_o$-treatment on high-$[K^+]_o$-induced bursting activity. Slices (n=12) were exposed to medium in which $[K^+]_o$ had been increased to 12 mM, and field potentials were recorded with a field electrode in the CA1 cell body layer. Spontaneous field potential bursting was observed for at least 20 minutes, and then the slices were exposed to medium in which $[K^+]_o$ was maintained at 12 mM, but $[Cl^-]_o$ was reduced to 21 mM. Within 15–20 minutes after the tissue was exposed to the low-$[Cl^-]_o$/high-$[K^+]_o$-medium, the burst amplitude increased and each field event had a longer duration. After a brief period of this facilitated field activity (lasting 5–10 minutes), the bursting stopped. To test whether this blockade was reversible, after at least 10 minutes of field potential silence, we switched back to high-$[K^+]_o$-medium with normal $[Cl^-]_o$. The bursting returned within 20–40 minutes. Throughout each experiment, the CA1 field response to Schaffer collateral stimulation was monitored. The largest field responses were recorded just before the cessation of spontaneous bursting, during the period when the spontaneous bursts had the largest amplitude. Even after the blockade of spontaneous bursting, however, multiple population spikes were elicited by Schaffer collateral stimulation, indicating that synaptic transmission was intact, and that the tissue remained hyperexcitable.

In four slices, intracellular recordings from CA1 pyramidal cells were acquired along with the CA1 field recording. During the period of high-$[K^+]_o$-induced spontaneous bursting, hyperpolarizing current was injected into the cell so that postsynaptic potentials (PSPs) could be better observed. After low-$[Cl^-]_o$-blockade of spontaneous bursting, spontaneously occurring action potentials and PSPs were still observed. These observations further support the view that synaptic activity, per se, was not blocked by the low-$[Cl^-]_o$ treatment.

EXAMPLE 10

Low-$[Cl^-]_o$-Blockade of Epileptiform Activity Induced by 4-AP, High-$[K^+]_o$, and Bicuculline in CA1 and CA3

We next tested whether low-$[Cl^-]_o$ treatment could block epileptiform activity in areas CA1 and CA3, which was elicited by different pharmacological treatments, as we had shown for furosemide treatment. For this set of experiments, we chose to test the effects of low-$[Cl^-]_o$ treatment on spontaneous bursting which had been induced by high-$[K^+]_o$ (12 mM) (n=5), 4-AP (100 μM) (n=4), and bicuculline (20 and 100 μM) (n=5). In each set of experiments, field responses were recorded simultaneously from areas CA1 and CA3, and in each case, the spontaneous epileptiform activity in both areas CA1 and CA3, was reversibly blocked within 30 minutes after $[Cl^-]_o$ in the perfusion medium had been reduced to 21 mM. These data suggest that, like furosemide, low-$[Cl^-]_o$ reversibly blocks spontaneous bursting in several of the most commonly studied in vitro models of epileptiform activity.

EXAMPLE 11

Comparison Between Low-$[Cl^-]_o$ and Furosemide on Blockade of High-$[K^+]_o$-Induced Epileptiform Activity The data from the previous sets of experiments are consistent with the hypothesis that the anti-epileptic effects of both low-$[Cl^-]_o$ and furosemide are mediated by their actions on the same physiological mechanisms. To further test this hypothesis, we compared the temporal sequence of effects of low-$[Cl^-]_o$ (n=12) and furosemide (2.5 and 5 mM) (n=4) on high-$[K^+]_o$-induced bursting, as recorded with a field electrode in CA1. We found that both low-$[Cl^-]_o$ and furosemide treatment induced a similar temporal sequence of effects: an initial brief period of increased amplitude of field activity, and then blockade (reversible) of spontaneous field activity. In both cases, electrical stimulation of the Schaffer collaterals elicited hyperexcited responses even after the spontaneous bursting had been blocked.

EXAMPLE 12

Consequences of Prolonged Exposure to Low-$[Cl-]_o$ Medium with Varied $[K+]_o$

In the preceding experiments, we monitored field activity in some slices for >1 hour after the spontaneous bursting had been blocked by low-$[Cl^-]_o$ exposure. After such prolonged low-$[Cl^-]_o$ exposure, spontaneous, long-lasting, depolarizing shifts developed. The morphology and frequency of these late-occurring field events appeared to be related to the extracellular potassium and chloride concentrations. Motivated by these observations, we performed a set of experiments in which we systematically varied $[Cl^-]_o$ and $[K^+]_o$ and observed the effects of these ion changes on the late-occurring spontaneous field events.

In our first set of experiments, slices were exposed to medium containing low-$[Cl]_o$ (7 mM) and normal-$[K^+]_o$ (3 mM) (n=6). After 50–70 minutes exposure to this medium, spontaneous events were recorded in area CA1; these events appeared as 5–10 mV negative shifts in the DC field, with the first episode lasting for 30–60 seconds. Each subsequent episode was longer than the previous one. This observation suggested that ion-homeostatic mechanisms were diminished over time as a result of the ion concentrations in the bathing medium. In some experiments (n=2) in which these negative DC field shifts had been induced, intracellular recordings from CA1 pyramidal cells were acquired simultaneously with the CA1 field recordings.

For these experiments, the intracellular and field recordings were acquired close to one another (<200 µm). Prior to each negative field shift (10–20 seconds), the neuron began to depolarize. Cellular depolarization was indicated by a decrease in resting membrane potential, an increase in spontaneous firing frequency, and a reduction of action potential amplitude. Coincident with the onset of the negative field shifts, the cells became sufficiently depolarized so that they were unable to fire spontaneous or current-elicited (not shown) action potentials. Since neuronal depolarization began 10–20 seconds prior to the field shift, it may be that a gradual increase in extracellular potassium resulted in the depolarization of a neuronal population, thus initiating these field events. Such an increase in $[K^+]_o$ might be due to alterations of the chloride-dependent glial cotransport mechanisms that normally move potassium from extracellular to intracellular spaces. To test whether increases in $[K+]_o$ preceded these negative field shifts (and paralleled cellular depolarization), experiments (n=2) were performed in which a $K^+$-selective microelectrode was used to record changes in $[K^+]_o$.

In each experiment, the $K^+$-selective microelectrode and a field electrode were placed in the CA1 pyramidal layer close to one another (<200 µm), and a stimulation pulse was delivered to the Schaffer collaterals every 20 seconds so that the magnitude of the population spike could be monitored. Multiple spontaneously occurring negative field shifts were evoked by perfusion with low-[Cl⁻o] (7 mM) medium. Each event was associated with a significant increase in $[K^+]_o$, with the $[K^+]_o$ increase starting several seconds prior to the onset of negative field shift. A slow 1.5–2.0 mM increase in $[K^+]_o$ occurred over a time interval of approximately 1–2 minute seconds prior to the onset of each event. The stimulation-evoked field responses slowly increased in amplitude over time, along with the increasing $[K^+]_o$, until just before the negative field shift.

In a second set of experiments (n=4), $[K^+]_o$ was increased to 12 mM and $[Cl^-]_o$ was increased to 16 mM. After 50–90 minutes exposure to this medium, slow oscillations were recorded in area CA1. These oscillations were characterized by 5–10 mV negative DC shifts in the field potential and had a periodicity of approximately 1 cycle/40 seconds. Initially, these oscillations occurred intermittently and had an irregular morphology. Over time, these oscillations became continuous and developed a regular waveform. Upon exposure to furosemide (2.5 mM), the amplitude of the oscillations was gradually decreased and the frequency increased until the oscillations were completely blocked. Such low-$[Cl]_o$-induced oscillations in tissue slices have not been previously reported. However, the temporal characteristics of the oscillatory events bear a striking resemblance to the low-$[Cl]_o$-induced $[K^+]_o$ oscillations which were previously described in a purely axonal preparation.

In a third set of experiments (n=5) $[Cl^-]_o$ was further increased to 21 mM and $[K^+]_o$ was reduced back to 3 mM. In these experiments, single, infrequently occurring negative shifts of the field potential developed within 40–70 minutes (data not shown). These events (5–10 mV) lasting 40–60 seconds, occurred at random intervals, and maintained a relatively constant duration throughout the experiment. These events could sometimes be elicited by a single electrical stimulus delivered to the Schaffer collaterals.

Finally, in a final set of experiments (n=5), $[Cl^-]_o$ was kept at 21 mM and $[K^+]_o$ was raised to 12 mM. In these experiments, late-occurring spontaneous field events were not observed during the course of the experiments (2–3 hours).

EXAMPLE 13

Changes in $[K^+]_0$ During Low-Chloride Exposure

Sprague-Dawley adult rats were prepared as previously described. Transverse hippocampal slices, 400 µm thick, were cut with a vibrating cuter and stored in an oxygenated holding chamber for 1 hour before recording. A submersion-type chamber was used for $K^+$-selective microelectrode recordings. Slices were perfused with oxygenated (95% $O_2$–5% $CO_2$) artificial cerebrospinal fluid (ACSF) at 34–35° C. Normal ACSF contained 10 mM dextrose, 124 mM NaCl 3 mM KCl, 1.25 mM $NaH_2PO_4$, 1.2 mM $MgSO_4$, 26 mM $NaHCO_3$ and 2 mM $CaCl_2$. In some experiments, normal or low-chloride medium was used containing 4-aminopyridine (4-AP) at 100 µM. Low-chloride solutions (21 mM $[Cl]_0$) were prepared by equimolar replacement of NaCl with Na+-gluconate (Sigma Chemical Co.).

Field recordings from the CA1 or CA3 cell body layers were acquired with low-resistance glass electrodes filled with NaCl (2M). For stimulation of the Schaffer collateral pathway, a monopolar stainless-steel electrode was placed on the surface of the slide midway between areas CA1 and CA3. All recordings were digitized (Neurorocorder, Neurodata Instruments, New York, N.Y.) and stored on videotape.

$K^+$ selective microelectrodes were fabricated according to standard methods. Briefly, the reference barrel of a double-barreled pipette was filled with ACSF, and the other barrel was sylanized and the tip back-filled with KCl with $K^+$-selective resin (Coming 477317). Ion-selective microelectrodes were calibrated and considered suitable if they had a Nernstian slope response and remained stable throughout the duration of the experiment.

Exposure of hippocampal slices to low-[Cl–]₀ medium has been shown to include a temporally-dependent sequence of changes on the activity of CA1 pyramidal cells, with three characteristics phases, as described above. In brief, exposure to low-[Cl–]₀ medium results in a brief period of increased hyperexcitability and spontaneous epileptiform discharge. With further exposure to low-$[Cl^-]_0$ medium, spontaneous epileptiform activity is blocked, but cellular hyperexcitability remains, and action potential firing times become less synchronized with one another. Lastly, with prolonged exposure, the action potential firing times become sufficiently desynchronized so that stimulation-evoked field responses completely disappear, yet individual cells continue to show monosynapticlly-evoked responses to Schaffer collateral stimulation. The following results demonstrate that the anti-epileptic effects of furosemide on chloride-cotransport antagonism are independent of direct actions on excitatory synaptic transmission, and are a consequence of a desynchronization of population activity with our any associated decrease in excitability.

In six hippocampal slices, $K^+$-selective and field microelectrodes were placed in the CA1 cell body layer, and a stimulating electrode was placed on the Schaffer collateral pathway, and single-pulse stimuli (300 µs) were delivered every 20 seconds (FIG. 19). After stable baseline $[K^+]_o$ was observed for at least 20 minutes, the perfusion was switched to low-$[Cl^-]_o$ medium. Within 1–2 minutes of exposure to low-$[Cl^-]_o$ medium, the field responses became hyperexcitable as the $[K^+]_o$ began to rise. After approximately 4–5 minutes of exposure to low-$[Cl^-]_o$ medium the magnitude of the field response diminished, until it was completely abolished. The corresponding recording of $[K^+]_o$ showed that potassium began to rise immediately after exposure to low-$[Cl^-]_o$ medium, and that the peak of this $[K^+]_o$ rise corresponded in time to the maximally hyperexcitable CA1 field response. Coincident with the reduction of the magnitude of the field response, the $[K^+]_o$ began to diminish until after 8–10 minutes exposure to low-$[Cl^-]_o$ medium, it became constant for the remainder of the experiment at 1.8–2.5 mM above control levels. Four slices were switched back to control medium and allowed to fully recover. The experiment was then repeated with the $K^+$-selective microelectrode placed in the stratum radiatum. A similar sequence of changes in $[K^+]_o$ was observed in the dendritic layer, with the values of $[K^+]_o$ being 0.2–0.3 mM less than those observed in the cell body layers.

In four hippocampal slices, the responses of stimulation-evoked changes in $[K^+]_o$ between control conditions and after the CA1 field response was completely abolished by low-$[Cl^-]_o$ exposure were compared. In each slice, the $[K^+]_o$-selective measurements were acquired first in the cell body layer, and then after allowance for complete recovery in control medium, the experiment was repeated with the $K^+$-selective electrode moved to the stratum radiatum. Each stimulation trial consisted of a 10 Hz volley delivered to the Schaffer collateral for 5 seconds. The peak rises in $[K^+]_o$ were similar between control conditions an after prolonged exposure to low-$[Cl^-]_o$ medium, and between the cell body and dendritic layers. However, the recovery times observed after prolonged exposure to low-$[Cl^-]_o$ were significantly longer than those observed during control conditions.

These results demonstrate that the administration of furosemide resulted in increased $[K^+]_o$ in the extracellular spaces. Exposure of the brain tissue to low-$[Cl^-]_o$ medium immediately induced a rise in $[K^+]_o$ by 1–2 mM, which remained throughout the duration of exposure, and was coincident with the initial increase in excitability and the eventual abolishment of the CA1 field response. This loss of CA1 field response during low-$[Cl^-]_o$ exposure is most likely due to the desynchronization of neuronal firing times. Significantly, the stimulation-evoked increases in $[K^+]_o$, in both the cell body and dendritic layers were nearly identical before and after the complete low-$[Cl^-]_o$ blockade of the CA1 field response. This data suggests that comparable stimulation-evoked synaptic drive and action potential generation occurred under control conditions and after low-$[Cl^-]_o$ blockade of the field. Together these data demonstrate that the antiepileptic and desynchronizing effects of the chloride-cotransport antagonist, furosemide, are independent of direct actions on excitatory synaptic transmission and are a consequence of a desynchronization of population activity without decrease in excitability.

EXAMPLE 14

Changes in Extracellular pH During Low-Chloride Exposure

Antagonists of the anion/chloride-dependent cotransporter, such as furosemide and low-$[Cl-]_o$, may affect extracellular pH transients that might contribute to the maintenance of synchronized population activity. Rat hippocampal brain slices were prepared as described in Example 13, except the $NaHCO_3$ was substituted by equimolar amount of HEPES (26 nM) and an interface-type chamber was used.

In four hippocampal brain slices continuous spontaneous bursting was elicited by exposure to medium containing 100 µM 4-AP, as described in Example 13. Field recordings were acquired simultaneously from the cell body layers in areas CA1 and CA3. A stimulus delivered every 30 seconds to the Schaffer collaterals throughout the duration of the experiments. After at least 20 minutes of continuous bursting was observed, the slices were exposed to nominally bicarbonate free, 4-AP-containing HEPES medium. There were no significant changes observed in the spontaneous or stimulation-evoked field responses resulting from prolonged exposure (0.2 hours) to HEPES medium. After the slices had been exposed for at least 2 hours to the HEPES medium, the perfusion was switched to 4-AP-containing HEPES medium in which the $[Cl^-]_o$ had been reduced to 21 mM. Exposure to the low-$[Cl^-]_o$ HEPES medium induced the identical sequences of events, and at the same time course, as had previously been observed with low-$[Cl^-]_o$ $NaHCO_3$-containing medium. After complete blockade of spontaneous bursting, the perfusion medium was switched back HEPES medium with normal $[Cl^-]_o$. Within 20–40 minutes, spontaneous bursting resumed. At the time the spontaneous bursting had resumed, the slices had been perfused with nominally bicarbonate-free HEPES medium for greater than 3 hours.

This data suggests that the actions of chloride-cotransport antagonism on synchronization and excitability are independent of affects on the dynamics of extracellular pH.

Figure 4A:
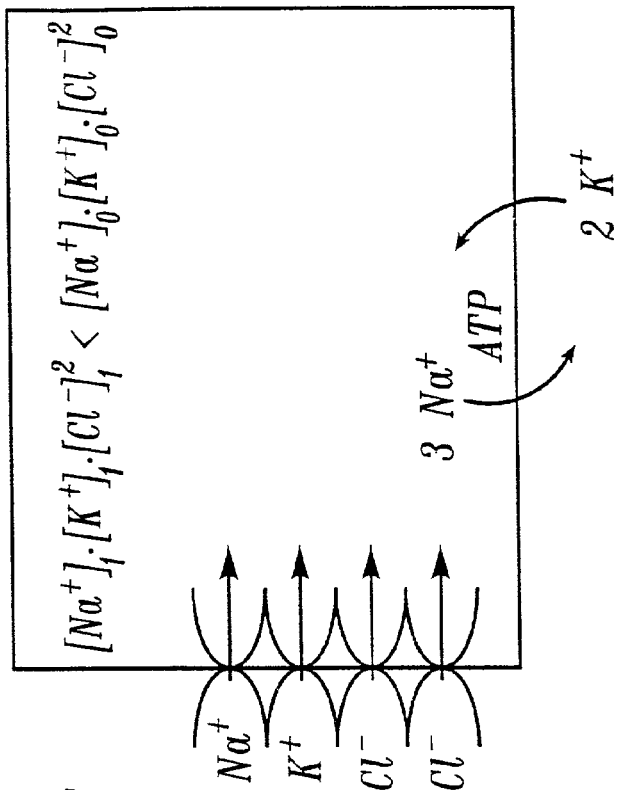
FIGS. 4A and 4B show a schematic diagram of ion cotransport under conditions of reduced chloride concentration.
Figure 4A:
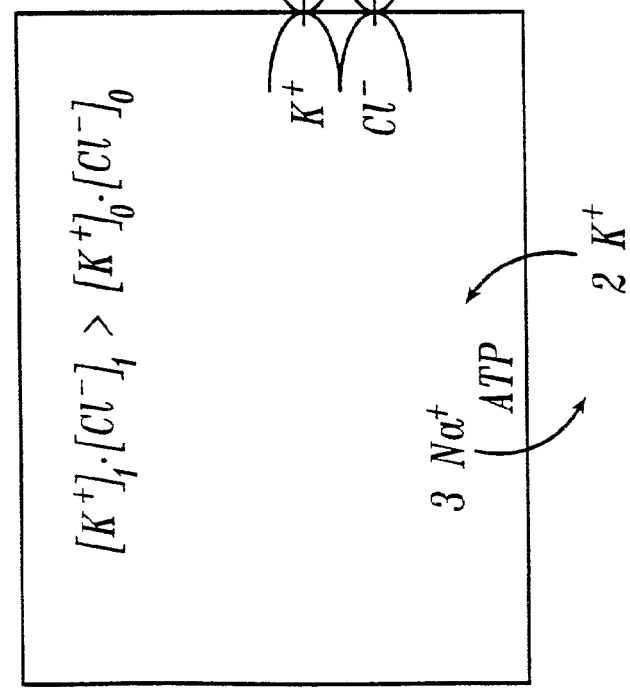

FIG. 4 illustrates a schematic model of ion cotransport under conditions of reduced $[Cl^-]$. FIG. 4A, left panel, shows that the chloride gradient necessary for the generation of IPSPs in neurons is maintained by efflux of ions through a furosemide-sensitive $K^+$, $Cl^-$ cotransporter. Under normal conditions, a high concentration of intracellular potassium (maintained by the $3Na^+$, $2K^+$-ATPase pump) serves as the driving force for the extrusion of $Cl^-$ against its concentration gradient. In glial cells, as shown in the right panel of FIG. 4A, the movement of ions through the furosemide-sensitive $Na^+$, $K^+$, $2Cl^-$-cotransporter is from extracellular to intracellular spaces. The ion-gradients necessary for this cotransport are maintained, in part, by the "transmembrane sodium cycle": sodium ions taken into glial cells through $Na^+$, $K^+$, $2Cl^-$-cotransport are continuously extruded by the $3Na^+$, $2K^+$-ATPase pump so that a low intracellular sodium concentration is maintained. The rate and direction of ion-flux through the furosemide-dependent cotransporters are functionally proportional to their ion-product differences written as $[K^+]_i \times [Cl^-]_i - [K^+]_o \times [Cl^-]_o$) for neuronal $K^+$, $Cl^-$ cotransport and as $[Na^+]_i \times [K^+]_i \times [Cl^-]^2_i - [Na^+]_o \times [K^+]_o \times [Cl^-]^2_o$) for glial $Na^+$, $K^+$, $2Cl^-$ cotransport. The sign of these ion-product differences show the direction of ion transport with positive being from intracellular to extracellular spaces.

Figure 4B:
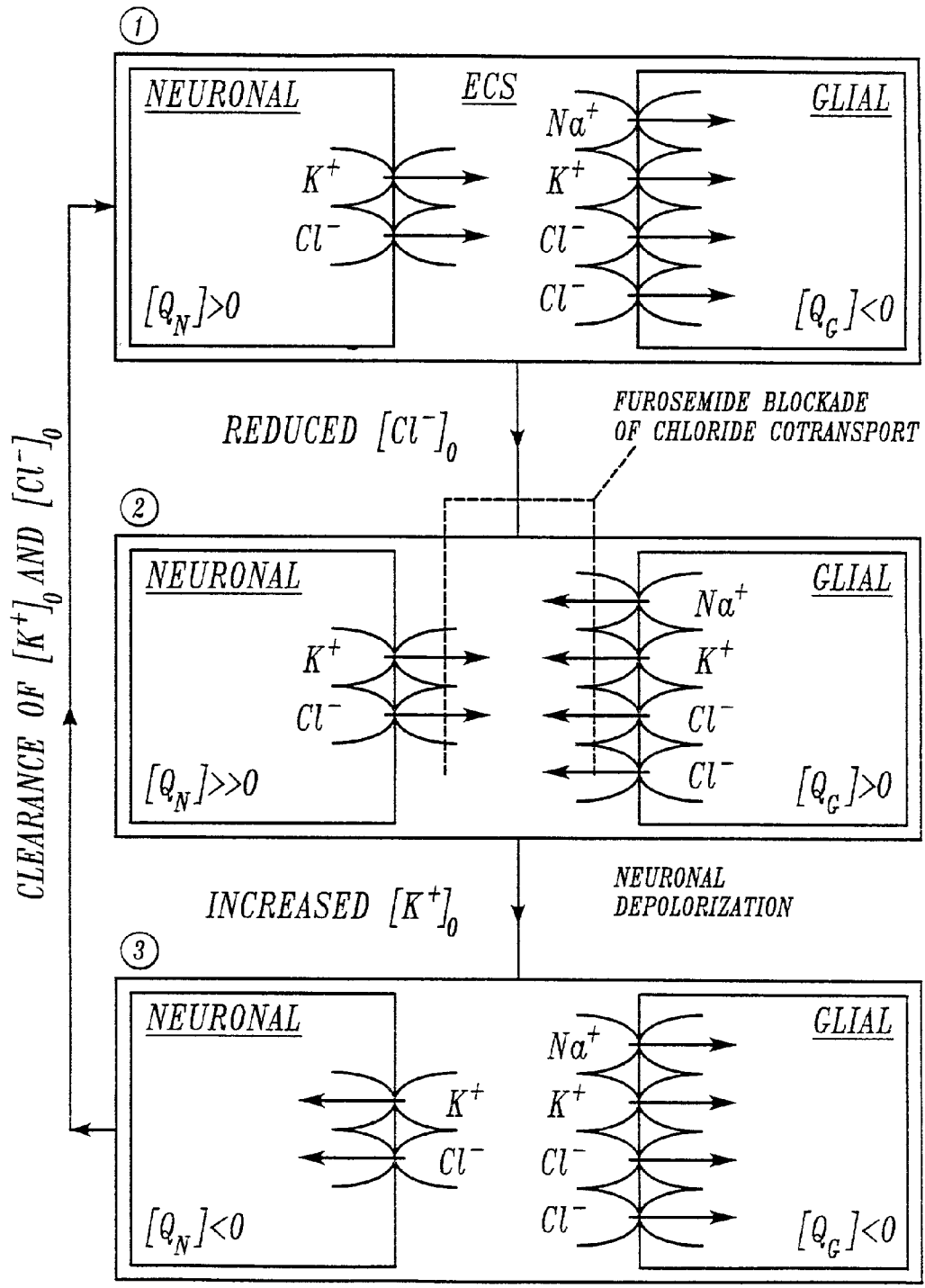

FIG. 4B shows a schematic phenomenological model that explains the emergence of the late-occurring spontaneous field events that arise as a result of prolonged low $-[Cl^-]_o$ exposure. We denote the ion-product differences for neurons and glia as $Q_N$ and $Q_G$, respectively. Under control conditions (1), the differences of the ion-products for neurons are such that $K^+$ and $Cl^-$ are cotransported from intracellular to extracellular spaces ($Q_N>0$); the differences in ion-products for glial cells are such that $Na^+$, $K^+$ and $Cl^-$ are cotransported from the ECS to intracellular compartments ($Q_G<0$). When $[Cl^-]_o$ is reduced (2), the ion-product differences are altered so that neuronal efflux of KCl is increased; however, the glial icon cotransport is reversed ($Q_G>0$), s that there is a net efflux of KCl and NaCl from intracellular to extracellular spaces. These changes result in buildup of extracellular potassium over time. Eventually, $[K^+]_o$ reaches a level that induces the depolarization of neuronal populations, resulting in an even larger accumulation of $[K^+]_o$. This large accumulation of extracellular ions then serves to reverse the ion-product differences so that KCl is moved from extracellular to intracellular spaces ($Q_N<0$, $Q_G<0$) (3). Further clearance of the extracellular potassium eventually resets the transmembrance ion gradients to initial conditions. By cycling through this process, repetitive negative field events are generated.

All patents and publications cited herein and PCT Application WO 00/37616, published Jun. 29, 2000, are specifically incorporated by reference herein in their entireties.

I claim:

1. A method for treating migraine headaches without aura in a human subject in need thereof, comprising administering an effective amount of a composition consisting essentially of a $Na^+K^+2Cl^-$ cotransporter antagonist that is capable of inhibiting $Na^+K^+2Cl^-$ cotransport in glial cells to the subject, wherein said $Na^+K^+2Cl^-$ cotransporter antagonist is selected from the group consisting of furosemide and bumetanide.

2. The method of claim 1, wherein the $Na^+K^+2Cl^-$ cotransporter antagonist blocks spontaneous synchronized depolarizing oscillations of neuronal population activity in the central nervous system.

3. The method of claim 1, wherein the $Na^+K^+2Cl^-$ cotransporter antagonist produces modulation of the chloride concentration in extracellular space in the central nervous system.

4. The method of claim 1, wherein the $Na^+K^+2Cl^-$ cotransporter antagonist is administered intranasally.

5. The method of claim 1, wherein the $Na^+K^+2Cl^-$ cotransporter antagonist is administered directly into the cerebrospinal fluid.

6. The method of claim 1, wherein the treatment composition is administered transdermally for delivery to the CNS.

7. The method of claim 1, wherein the composition is administered in a sustained release formulation.

8. The method of claim 1, wherein the composition is delivered in a liposome formulation.

* * * * *